(12) United States Patent
Yuan et al.

(10) Patent No.: US 8,652,480 B2
(45) Date of Patent: Feb. 18, 2014

(54) **SHORTENED PURIFICATION PROCESS FOR THE PRODUCTION OF CAPSULAR *STREPTOCOCCUS PNEUMONIAE* POLYSACCHARIDES**

(75) Inventors: Yonghui Yuan, Tappan, NY (US); Mark Ruppen, Garnerville, NY (US); Wei-Qiang Sun, Morristown, NJ (US); Ling Chu, Suffern, NY (US); John Simpson, Upper Nyack, NY (US); James Patch, Cornwall on Hudson, NY (US); Justin Keith Moran, Valley Cottage, NY (US); Pamela Fink, New City, NY (US)

(73) Assignee: Wyeth LLC, Madison, NJ (US)

( * ) Notice: Subject to any disclaimer, the term of this patent is extended or adjusted under 35 U.S.C. 154(b) by 549 days.

(21) Appl. No.: 12/052,525

(22) Filed: Mar. 20, 2008

(65) Prior Publication Data

US 2008/0286838 A1    Nov. 20, 2008

Related U.S. Application Data

(60) Provisional application No. 60/896,616, filed on Mar. 23, 2007.

(51) Int. Cl.
*A61K 31/70* (2006.01)
*A61K 39/00* (2006.01)

(52) U.S. Cl.
USPC .......................................... 424/184.1; 514/23

(58) Field of Classification Search
None
See application file for complete search history.

(56) References Cited

U.S. PATENT DOCUMENTS

| | | | |
|---|---|---|---|
| 4,221,906 A * | 9/1980 | Querry et al. ................. 536/127 |
| 4,686,102 A * | 8/1987 | Ritchey et al. ............. 424/244.1 |
| 5,623,057 A | 4/1997 | Marburg et al. |
| 5,714,354 A * | 2/1998 | Arnold et al. ................. 435/101 |
| 6,146,902 A * | 11/2000 | McMaster ..................... 436/177 |
| 7,709,001 B2 * | 5/2010 | Hausdorff et al. .......... 424/184.1 |
| 7,718,791 B2 * | 5/2010 | Bahler et al. ................ 536/127 |
| 2006/0228380 A1 | 10/2006 | Hausdorff et al. |
| 2006/0228381 A1 | 10/2006 | Bahler et al. |

FOREIGN PATENT DOCUMENTS

| EP | 0 002 004 A1 | 6/1979 |
|---|---|---|
| EP | 1 762 245 A2 | 3/2007 |
| WO | WO 82/01995 | 6/1982 |

OTHER PUBLICATIONS

Katzenellenboegen et al. Carbohydrate Res. 124: 235-245, 1983.*
Henrichsen et al. FEMS Microbiol. Lett. 94: 89-94, 1992.*
Goncalves et al., "Purification of capsular polysaccharide from *Streptococcus pneumoniae* serotype 23F by a procedure suitable for scale-up," Biotechnology and Applied Biochemistry, 37(Pt.3):283-287 (2003).

* cited by examiner

*Primary Examiner* — Albert Navarro
(74) *Attorney, Agent, or Firm* — Royal N. Ronning, Jr.

(57) ABSTRACT

A shortened process for producing a solution containing substantially purified capsular polysaccharides from a cellular *Streptococcus pneumoniae* lysate broth is described. Ultrafiltering and diafiltering a clarified *S. pneumoniae* lysate followed by pH adjustment to less than 4.5, preferably about 3.5, precipitated at least 98% of the protein in the solution without seriously affecting polysaccharide yield. Furthermore, following ultrafiltration and diafiltration and acidification to a pH of less than 4.5, filtration using activated carbon precipitated at least 90% of remaining protein without seriously affecting polysaccharide yield. Exemplary, non-limiting *S. pneumoniae* serotypes that can be purified using the shortened process of the invention are 1, 4, 5, 6A, 6B, 7F, 9V, 14, 18C, 19A, 19F, and 23F. In one embodiment, the *Streptococcus pneumoniae* cells are lysed using deoxycholate sodium (DOC), while in another embodiment the lytic agent is a non-animal derived lytic agent such as N-lauryl sarcosine sodium (NLS).

3 Claims, 15 Drawing Sheets

SHORTENED PURIFICATION PROCESS FOR THE PRODUCTION OF CAPSULAR STREPTOCOCCUS PNEUMONIAE POLYSACCHARIDES

This application claims priority under 35 U.S.C. §119(e) from U. S. Provisional Application No. 60/896,616, filed Mar. 23, 2007, the entire disclosure of which is incorporated by reference herein.

FIELD OF THE INVENTION

This invention relates to methods for removing excess soluble protein and other impurities from cellular lysates of Streptococcus pneumoniae (*S. pneumoniae*) serotypes used in the production of purified pneumococcal polysaccharides.

BACKGROUND OF THE INVENTION

*Streptococcus pneumoniae* are Gram-positive, lancet shaped cocci that are usually seen in pairs (diplococci), but also in short chains or as single cells. They grow readily on blood agar plates with glistening colonies and display alpha hemolysis unless grown anaerobically where they show beta hemolysis. They are sensitive to bile salts that can break down the cell wall with the presence of the cells' own enzyme, autolysin. The organism is an aerotolerant anaerobe and is fastidious in that it has complex nutritional requirements.

The cells of most pneumococcal serotypes have a capsule which is a polysaccharide coating surrounding each cell. This capsule is a determinant of virulence in humans because it interferes with phagocytosis by preventing antibodies from attaching to the bacterial cells. There are currently 90 capsular serotypes identified, with 23 serotypes responsible for about 90% of invasive disease. As a vaccine the polysaccharide can confer a reasonable degree of immunity to *S. pneumoniae* in individuals with developed or unimpaired immune systems. However, when the polysaccharide is conjugated with a high molecular weight protein such as $CRM_{197}$ and formulated into a vaccine containing conjugates of multiple serotypes, such conjugate vaccines allow for an immune response in infants and elderly who are also most at risk for pneumococcal infections.

The capsular polysaccharide for each *S. pneumoniae* serotype utilized for vaccine products is produced by growing the organism in liquid medium. The population of the organism is often scaled up from a seed vial to seed bottles and passed through one or more seed fermentors of increasing volume until production scale fermentation volumes are reached. The end of the growth cycle can be determined by one of several means, at which point the cells are lysed through the addition of a detergent or other reagent which aids in the cell wall breakdown and release of autolysin which causes cellular lysis when the cells reach stationary phase. The broth is then harvested for downstream (purification) processing. The major contaminants are cellular proteins, nucleic acids, C-polysaccharide and medium components.

For most of the serotypes for the currently marketed 7-valent pneumococcal conjugate (7vPnC) vaccine (PREVNAR®), as well as the newly developed 13-valent pneumococcal conjugate (13vPnC) vaccine, the current purification process requires sixteen steps involving many expensive, labor intensive and technologically demanding operations, such as chromatography and multiple membrane separations. Previous attempts at improving purification processes for *S. pneumoniae* polysaccharides have included, for example, pH manipulation during fermentation and recovery (see U.S. Patent App. Pub. No. 2006/0228381) and solvent and detergent precipitation. However, the removal of impurities in these processes is still spread over many labor intensive and costly steps. Protein level is the most problematic specification to meet due to the physical and chemical properties of the soluble proteins.

Thus, there is a need for a simplified purification process to reduce the soluble protein levels in *S. pneumoniae* lysates and eliminate inefficiencies of the current purification process to produce substantially purified capsular polysaccharides suitable for incorporation into pneumococcal conjugate vaccines.

SUMMARY OF THE INVENTION

The present invention relates to a process for producing a solution containing substantially purified capsular polysaccharides from a *Streptococcus pneumoniae* cell lysate. This process comprises the steps of:

(a) providing a fermentation broth comprising bacterial cells that produce a selected *Streptococcus pneumoniae* serotype;

(b) lysing the bacterial cells in step (a) with a lytic agent, thereby producing a cell lysate comprising cell debris, soluble proteins, nucleic acids, and polysaccharides;

(c) clarifying the cell lysate of step (b) using centrifugation or filtration to remove cell debris, thereby producing a clarified cell lysate;

(d) ultrafiltering and diafiltering the clarified cell lysate of step (c) to remove low molecular weight impurities and increase polysaccharide concentration, thereby producing a retentate;

(e) lowering the pH of the retentate of step (d) to less than 4.5 to precipitate protein and nucleic acids, thereby forming an acidified retentate solution;

(f) holding the acidified retentate solution formed in step (e) for a time sufficient to allow settling of the precipitate, followed by filtration or centrifugation of the acidified retentate solution, thereby producing a clarified polysaccharide solution;

(g) filtering the clarified polysaccharide solution of step (f) through an activated carbon filter;

(h) ultrafiltering and diafiltering the filtered solution produced by step (g), thereby producing a concentrated purified polysaccharide solution; and (i) filtering the concentrated purified polysaccharide solution produced by step (h) using a sterile filter;

whereby a solution containing substantially purified capsular polysaccharides is produced. Exemplary, non-limiting *S. pneumoniae* serotypes selected for this embodiment of the invention are 1, 4, 5, 6A, 6B, 7F, 9V, 14, 18C, 19A, 19F, and 23F. In a particular embodiment, the pH of step (e) is lowered to about 3.5. In another embodiment, the diafiltration of step (h) comprises a pH adjustment to between about 5.5 to about 7.5. In another embodiment, the diafiltration of step (h) comprises a pH adjustment to between about 7.0 to about 7.5. In another embodiment, the diafiltration of step (h) comprises a pH adjustment to about 7.4. In still another embodiment, step (e) removes at least 98% of protein from the retentate of step (d). In another embodiment, step (g) removes at least 90% of the protein from the clarified polysaccharide solution of step (f). In another embodiment, the activated carbon filter of step (g) comprises wood-based phosphoric acid-activated carbon. In another embodiment, step (f) comprises holding the acidified retentate solution formed in step (e) for at least 2 hours. In still another embodiment, the lytic agent of step (b) is deoxycholate sodium (DOC). In another embodiment, the lytic agent of step (b) is a non-animal derived lytic agent. In still another embodiment, the lytic agent of step (b) is the non-animal derived lytic agent N-lauryl sarcosine sodium (NLS).

The present invention also relates to a process for producing a solution containing substantially purified capsular polysaccharides from a *Streptococcus pneumoniae* cell lysate comprising serotype 1, 4, 5, 6A, 6B, 7F, 9V, 14, 18C, 19F, or 23F. This process comprises the steps of:

(a) providing a fermentation broth comprising bacterial cells that produce *Streptococcus pneumoniae* serotype 1, 4, 5, 6A, 6B, 7F, 9V, 14, 18C, 19F, or 23F;

(b) lysing the bacterial cells in step (a) with a lytic agent, thereby producing a cell lysate comprising cell debris, soluble proteins, nucleic acids, and polysaccharides;

(c) clarifying the cell lysate of step (b) using centrifugation or filtration to remove cell debris, thereby producing a clarified cell lysate;

(d) ultrafiltering and diafiltering the clarified cell lysate of step (c) at room temperature at neutral pH in salt free media to remove low molecular weight impurities and increase polysaccharide concentration, thereby producing a salt free retentate;

(e) lowering the pH of the salt free retentate of step (d) to less than 4.5 to precipitate protein and nucleic acids, thereby forming an acidified retentate solution;

(f) holding the acidified retentate solution formed in step (e) for at least 2 hours at room temperature to allow settling of the precipitate, followed by filtration or centrifugation of the acidified retentate solution, thereby producing a clarified polysaccharide solution;

(g) filtering the clarified polysaccharide solution of step (f) through an activated carbon filter;

(h) ultrafiltering and diafiltering the filtered solution produced by step (g), thereby producing a concentrated purified polysaccharide solution; and (i) filtering the concentrated purified polysaccharide solution produced by step (h) using a sterile filter;

whereby a solution containing substantially purified capsular polysaccharides comprising serotype 1, 4, 5, 6A, 6B, 7F, 9V, 14, 18C, 19F, or 23F is produced. In a particular embodiment, the pH of step (e) is lowered to about 3.5. In another embodiment, the diafiltration of step (h) comprises a pH adjustment to between about 5.5 to about 7.5. In another embodiment, the diafiltration of step (h) comprises a pH adjustment to between about 7.0 to about 7.5. In another embodiment, the diafiltration of step (h) comprises a pH adjustment to about 7.4. In still another embodiment, step (e) removes at least 98% of protein from the salt free retentate of step (d). In another embodiment, step (g) removes at least 90% of the protein from the clarified polysaccharide solution of step (f).

In another embodiment, the activated carbon filter of step (g) comprises wood-based phosphoric acid-activated carbon. In still another embodiment, the lytic agent of step (b) is deoxycholate sodium (DOC). In another embodiment, the lytic agent of step (b) is a non-animal derived lytic agent. In still another embodiment, the lytic agent of step (b) is the non-animal derived lytic agent N-lauryl sarcosine sodium (NLS).

The present invention also relates to a process for producing a solution containing substantially purified capsular polysaccharides from a *Streptococcus pneumoniae* cell lysate comprising serotype 19A. This process comprises the steps of:

(a) providing a fermentation broth comprising bacterial cells that produce *Streptococcus pneumoniae* serotype 19A;

(b) lysing the bacterial cells in step (a) with a lytic agent, thereby producing a cell lysate comprising cell debris, soluble proteins, nucleic acids, and polysaccharides;

(c) clarifying the cell lysate of step (b) using centrifugation or filtration to remove cell debris, thereby producing a clarified cell lysate;

(d) ultrafiltering and diafiltering the clarified cell lysate of step (c) at about 4° C. at a pH of about 6 in sodium phosphate buffer to remove low molecular weight impurities and increase polysaccharide concentration, thereby producing a retentate;

(e) lowering the pH of the retentate of step (d) to less than 4.5 to precipitate protein and nucleic acids, thereby forming an acidified retentate solution;

(f) holding the acidified retentate solution formed in step (e) for at least 2 hours at about 4° C. to allow settling of the precipitate, followed by filtration or centrifugation of the acidified retentate solution, thereby producing a clarified polysaccharide solution;

(g) adjusting the pH of the clarified polysaccharide solution of step (f) to about 6, thereby producing a pH-adjusted clarified polysaccharide solution;

(h) filtering the pH-adjusted clarified polysaccharide solution of step (g) through an activated carbon filter;

(i) ultrafiltering and diafiltering the filtered solution produced by step (h), thereby producing a concentrated purified polysaccharide solution; and (j) filtering the concentrated purified polysaccharide solution produced by step (i) using a sterile filter;

whereby a solution containing substantially purified capsular polysaccharides comprising serotype 19A is produced. In a particular embodiment, the pH of step (e) is lowered to about 3.5. In another embodiment, the diafiltration of step (i) comprises a pH adjustment to between about 5.5 to about 7.5. In another embodiment, the diafiltration of step (i) comprises a pH adjustment to between about 7.0 to about 7.5. In another embodiment, the diafiltration of step (i) comprises a pH adjustment to about 7.4. In still another embodiment, step (e) removes at least 98% of protein from the retentate of step (d). In another embodiment, step (h) removes at least 90% of the protein from the pH-adjusted clarified polysaccharide solution of step (g). In another embodiment, the activated carbon filter of step (h) comprises wood-based phosphoric acid-activated carbon. In another embodiment, the sodium phosphate buffer of step (d) is 25 mM sodium phosphate. In still another embodiment, the lytic agent of step (b) is deoxycholate sodium (DOC). In another embodiment, the lytic agent of step (b) is a non-animal derived lytic agent. In still another embodiment, the lytic agent of step (b) is the non-animal derived lytic agent N-lauryl sarcosine sodium (NLS).

DETAILED DESCRIPTION OF THE INVENTION

Figure 1:
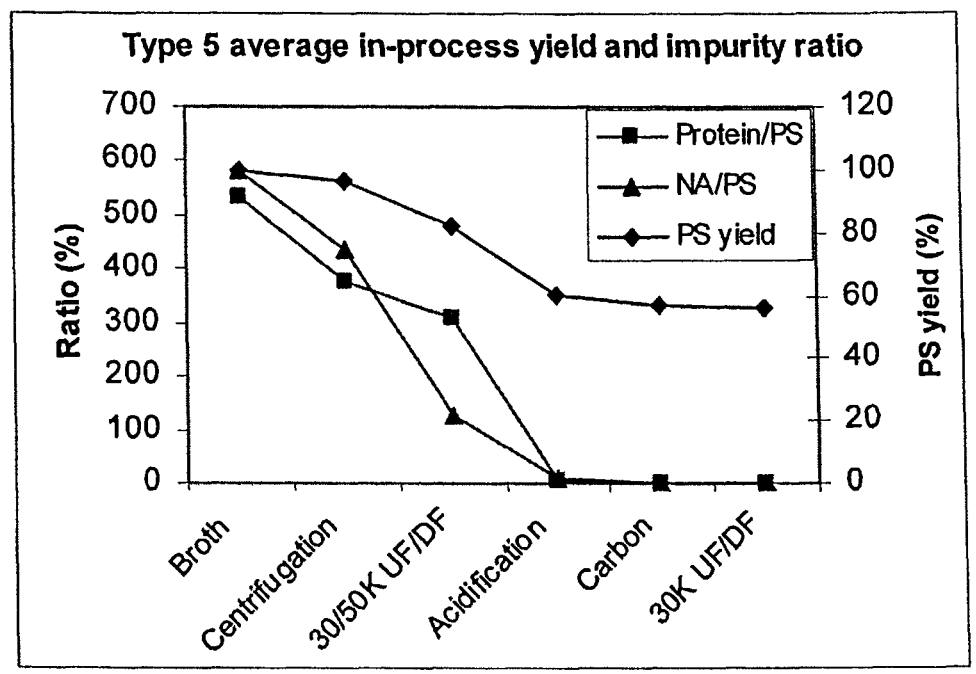
FIG. 1 shows average in-process polysaccharide (PS) yield, protein/PS ratio, and nucleic acid (NA)/PS ratio for serotype 5 using the shortened purification process of the invention. Results are shown for each purification step.

The present invention relates to a shortened purification process to reduce the soluble protein levels in cellular *Streptococcus pneumoniae* lysates to produce substantially purified capsular polysaccharides suitable for incorporation into pneumococcal conjugate vaccines. For most of the serotypes for the currently marketed 7-valent pneumococcal conjugate (7vPnC) vaccine (PREVNAR®), as well as the newly developed 13-valent pneumococcal conjugate (13vPnC) vaccine, the current polysaccharide purification process requires up to sixteen steps. These steps involve many expensive, labor-intensive, and technologically demanding operations, such as chromatography and multiple membrane separations. The process of the present invention eliminates up to eight of these steps while accomplishing the same purification and eliminates the need for chromatography. Thus, the present invention elates to a more efficient purification process that is less expensive, takes less time, and involves fewer steps.

The shortened purification process of the present invention relates to the discovery that ultrafiltering and diafiltering a clarified cellular *S. pneumoniae* lysate broth, followed by acidification of the concentrated lysate broth to a pH of less than 4.5, preferably about 3.5, precipitates at least 98% of the protein in the solution without seriously affecting polysaccharide yield. By ultrafiltering and diafiltering the lysed and clarified fermentation broth before acidification to a pH of less than 4.5, preferably around 3.5, "salting in" effects of proteins are eliminated and the fraction of protein that is "salted out" is increased. "Salting in" refers to increased solubility of proteins while "salting out" refers to precipitation of proteins in solution as they reach their isoelectric points. The ultrafiltration and diafiltration step also prevents the foaming observed when sodium-carbonate treated broth undergoes acidification even to a pH of 5.0 (see U.S. Patent App. Pub. No. 2006/0228381). Thus, ultrafiltration and diafiltration of the clarified lysate broth makes it possible to use any low molecular weight pH titrant such as sodium carbonate during *S. pneumoniae* serotype fermentation and prevents foaming of the clarified lysate broth when acidified to a pH of less than 4.5.

"Clarified lysate broth" refers to a lysate broth that has undergone centrifugation or filtration to remove cell debris.

"Diafiltering," "diafiltration," "DF," and like terms refer to, for example, using semi-permeable membranes with appropriate physical and chemical properties to remove small molecules from a solution.

"Ultrafiltering," "ultrafiltration," "UF," and like terms refer to, for example, using semi-permeable membranes with appropriate physical and chemical properties to discriminate between molecules in a solution and concentrate like molecules into a smaller volume of solution.

Within the methods of the present invention, ultrafiltration and diafiltration typically comprise "cross-flow" or "tangential-flow" filtration in order to avoid clogging of the filter membranes. In "cross-flow" filtration, the solution to be filtered is passed across the surface of the membrane. Materials which pass through the membrane are referred to as the permeate. The materials which do not pass through the membrane are referred to as the retentate. The retentate is recycled to a feed reservoir to be refiltered.

As used herein, any acid may be used to lower the pH of the ultrafiltered and diafiltered lysate broth so long as a pH of less than 4.5, particularly about 3.5, is achieved. Accordingly, both organic and mineral acids may be used within the methods of the invention. As used herein, the term "mineral acid" refers to an acid derived from inorganic mineral by chemical reaction as opposed to organic acids. Exemplary, non-limiting examples of mineral acids that may be used within the methods of the present invention include hydrochloric acid, nitric acid, phosphoric acid, and sulphuric acid. In particular embodiments, the pH of the concentrated lysate broth is lowered to less than 4.4, 4.3, 4.2, 4.1, 4.0, 3.9, 3.8, 3.7, 3.6, 3.5, 3.4, 3.3, 3.2, 3.1, or 3.0. In other embodiments, the pH of the concentrated lysate broth is lowered to about 4.4, about 4.3, about 4.2, about 4.1, about 4.0, about 3.9, about 3.8, about 3.7, about 3.6, about 3.5, about 3.4, about 3.3, about 3.2, about 3.1, about 3.0, about 2.9, about 2.8, about 2.7, about 2.6, about 2.5, about 2.4, about 2.3, about 2.2, about 2.1, or about 2.0.

The shortened purification process of the present invention also relates to the discovery that, in combination with the concentration and low pH steps described above, filtration using activated carbon precipitates at least 90% of remaining protein without seriously affecting polysaccharide yield. In particular embodiments, carbon filtration using carbon derived from sawdust or other wood products and activated with phosphoric acid was found to be more effective at reducing or removing protein impurities than carbons used within current carbon filtration methods.

Accordingly, the present invention relates to a process for producing a solution containing substantially purified capsular polysaccharides from a *Streptococcus pneumoniae* cell lysate comprising the steps of:

(a) providing a fermentation broth comprising bacterial cells that produce a selected *Streptococcus pneumoniae* serotype;

(b) lysing the bacterial cells in step (a) with a lytic agent, thereby producing a cell lysate comprising cell debris, soluble proteins, nucleic acids, and polysaccharides;

(c) clarifying the cell lysate of step (b) using centrifugation or filtration to remove cell debris, thereby producing a clarified cell lysate;

(d) ultrafiltering and diafiltering the clarified cell lysate of step (c) to remove low molecular weight impurities and increase polysaccharide concentration, thereby producing a retentate;

(e) lowering the pH of the retentate of step (d) to less than 4.5, particularly about 3.5, to precipitate protein and nucleic acids, thereby forming an acidified retentate solution;

(f) holding the acidified retentate solution formed in step (e) for a time sufficient to allow settling of the precipitate, particularly for at least 2 hours with or without agitation, followed by filtration or centrifugation of the acidified retentate solution, thereby producing a clarified polysaccharide solution;

(g) filtering the clarified polysaccharide solution of step (f) through an activated carbon filter, particularly an activated carbon filter comprising wood-based phosphoric acid-activated carbon;

(h) ultrafiltering and diafiltering the filtered solution produced by step (g), thereby producing a concentrated purified polysaccharide solution; and (i) filtering the concentrated purified polysaccharide solution produced by step (h) using a sterile filter;

whereby a solution containing substantially purified capsular polysaccharides is produced. The sterile filtration of step (i) is useful to remove bacteria and particles from the concentrated purified polysaccharide solution. Exemplary, non-limiting *S. pneumoniae* serotypes selected for this embodiment of the invention are 1, 4, 5, 6A, 6B, 7F, 9V, 14, 18C, 19A, 19F, and 23F. In a particular embodiment, step (e) removes at least 98% of protein from the retentate of step (d). In another embodiment, step (g) removes at least 90% of the protein from the clarified polysaccharide solution of step (f). In another embodiment, the diafiltration of step (h) comprises a pH adjustment to between about 5.5 to about 7.5. For improved stability of the substantially purified capsular polysaccharide during long-term storage, however, the diafiltration of step (h) comprises a pH adjustment to between about 7.0 to about 7.5, and more particularly to about 7.4.

As used herein, the term "substantially purified capsular polysaccharide-containing lysate" or "solution containing substantially purified capsular polysaccharides" refers to a cellular *Streptococcus pneumoniae* lysate or solution from which protein has been removed such that the percent ratio of protein to polysaccharide (protein/PS) is less than 10%, less than 9%, less than 8%, less than 7%, less than 6%, less than 5%, less than 4%, less than 3%, less than 2%, or less than 1% and the percent ratio of nucleic acid to polysaccharide (NA/PS) is less than 5%, less than 4%, less than 3%, less than 2%, or less than 1%. In particular embodiments, the percent ratios of protein/PS and NA/PS for substantially purified capsular polysaccharide-containing lysates or solutions comprising specific serotypes are as follows: for serotype 1 the ratio of protein/PS is less than 2% and the ratio of NA/PS is less than 2%, for serotype 4 the ratio of protein/PS is less than 3% and the ratio of NA/PS is less than 2%, for serotype 5 the ratio of protein/PS is less than or equal to 7.5% and the ratio of NA/PS is less than or equal to 2%, for serotype 6A the ratio of protein/PS is less than 2% and the ratio of NA/PS is less than 2%, for serotype 6B the ratio of protein/PS is less than 4% and the ratio of NA/PS is less than 1%, for serotype 7F the ratio of protein/PS is less than 5% and the ratio of NA/PS is less than 2%, for serotype 9V the ratio of protein/PS is less than 2% and the ratio of NA/PS is less than 1%, for serotype 14 the ratio of protein/PS is less than 3% and the ratio of NA/PS is less than 2%, for serotype 18C the ratio of protein/PS is less than 2% and the ratio of NA/PS is less than 2%, for serotype 19A the ratio of protein/PS is less than 2% and the ratio of NA/PS is less than 2%, for serotype 19F the ratio of protein/PS is less than 3% and the ratio of NA/PS is less than 2%, and for serotype 23F the ratio of protein/PS is less than 2% and the ratio of NA/PS is less than 2%. Methods for the quantification of protein, polysaccharide, and nucleic acid concentrations in a cellular lysate or solution are well known in the art and include, for example, SDS-PAGE (Sodium Dodecyl Sulfate Polyacrylamide Gel Electrophoresis) analysis, HPLC (High Performance Liquid Chromatography) and SEC (Size Exclusion Chromatography), modified Lowry assays, spectrophotometry, SEC-MALLS (Size-Exclusion Chromatography/Multi-Angle Laser Light Scattering), and NMR (Nuclear Magnetic Resonance).

Within the methods of the present invention, the bacterial cells may be lysed using any lytic agent. A "lytic agent" is any agent that aids in cell wall breakdown and release of autolysin which causes cellular lysis including, for example, detergents. As used herein, the term "detergent" refers to any anionic or cationic detergent capable of inducing lysis of bacterial cells. Representative examples of such detergents for use within the methods of the present invention include deoxycholate sodium (DOC), N-lauryl sarcosine (NLS), chenodeoxycholic acid sodium, and saponins.

In one embodiment of the present invention, the lytic agent used for lysing bacterial cells is DOC. DOC is the sodium salt of the bile acid deoxycholic acid, which is commonly derived from biological sources such as cows or oxen. DOC activates the LytA protein, which is an autolysin that is involved in cell wall growth and division in *Streptococcus pneumoniae*. The LytA protein has choline binding domains in its C-terminal portion, and mutations of the lytA gene are known to produce LytA mutants that are resistant to lysis with DOC.

Although there is no evidence that the use of DOC during *Streptococcus pneumoniae* polysaccharide purification poses a health risk, the use of such biologically derived reagents could raise potential regulatory concerns. Accordingly, in one embodiment of the present invention, the lytic agent used for lysing bacterial cells is a non-animal derived lytic agent. Non-animal derived lytic agents for use within the methods of the present invention include agents from non-animal sources with modes of action similar to that of DOC (i.e., that affect LytA function and result in lysis of *Streptococcus pneumoniae* cells). Such non-animal derived lytic agents include, but are not limited to, analogs of DOC, surfactants, detergents, and structural analogs of choline, and may be determined using procedures as described in the Experimental section herein below. In one embodiment, the non-animal derived lytic agent is selected from the group consisting of decanesulfonic acid, tert-octylphenoxy poly(oxyethylene)ethanols (e.g. IGEPAL® CA-630, CAS #: 9002-93-1, available from Sigma Aldrich, St. Louis, Mo.), octylphenol ethylene oxide condensates (e.g. TRITON® X-100, available from Sigma Aldrich, St. Louis, Mo.), N-lauryl sarcosine sodium (NLS), lauryl iminodipropionate, sodium dodecyl sulfate, chenodeoxycholate, hyodeoxycholate, glycodeoxycholate, taurodeoxycholate, taurochenodeoxycholate, and cholate. In another embodiment, the non-animal derived lytic agent is NLS.

The present invention also relates to serotype-specific modifications to the process described above. For example, because the serotype 19A polysaccharide is unstable and its molecular weight changes during purification, it was discovered that modifications to the process described were useful in stabilizing the 19A polysaccharide. These modifications included carrying out the ultrafiltration and diafiltration step prior to acidification at about 4° C. at a pH of about 6 in sodium phosphate buffer, holding the acidified retentate solution for at least 2 hours at about 4° C. to allow settling of the precipitate, and adjusting the pH of the clarified polysaccharide solution to 6 prior to the activated carbon filtration step. By contrast, it was discovered that for serotypes 1, 4, 5, 6A, 6B, 7F, 9V, 14, 18C, 19F, and 23F, less polysaccharide loss and more protein removal was achieved when the ultrafiltration and diafiltration step prior to acidification was carried out in salt free media such as water, and this step could be carried out at room temperature at neutral pH.

Accordingly, the present invention also relates to a process for producing a solution containing substantially purified capsular polysaccharides from a *Streptococcus pneumoniae* cell lysate comprising serotype 1, 4, 5, 6A, 6B, 7F, 9V, 14, 18C, 19F, or 23F comprising the steps of:

(a) providing a fermentation broth comprising bacterial cells that produce *Streptococcus pneumoniae* serotype 1, 4, 5, 6A, 6B, 7F, 9V, 14, 18C, 19F, or 23F;

(b) lysing the bacterial cells in step (a) with a detergent, thereby producing a cell lysate comprising cell debris, soluble proteins, nucleic acids, and polysaccharides;

(c) clarifying the cell lysate of step (b) using centrifugation or filtration to remove cell debris, thereby producing a clarified cell lysate;

(d) ultrafiltering and diafiltering the clarified cell lysate of step (c) at room temperature at neutral pH in salt free media to remove low molecular weight impurities and increase polysaccharide concentration, thereby producing a salt free retentate;

(e) lowering the pH of the salt free retentate of step (d) to less than 4.5, particularly about 3.5, to precipitate protein and nucleic acids, thereby forming an acidified retentate solution;

(f) holding the acidified retentate solution formed in step (e) for at least 2 hours at room temperature with or without agitation to allow settling of the precipitate, followed by filtration or centrifugation of the acidified retentate solution, thereby producing a clarified polysaccharide solution;

(g) filtering the clarified polysaccharide solution of step (f) through an activated carbon filter, particularly an activated carbon filter comprising wood-based phosphoric acid-activated carbon;

(h) ultrafiltering and diafiltering the filtered solution produced by step (g), thereby producing a concentrated purified polysaccharide solution; and (i) filtering the concentrated purified polysaccharide solution produced by step (h) using a sterile filter;

whereby a solution containing substantially purified capsular polysaccharides comprising serotype 1, 4, 5, 6A, 6B, 7F, 9V, 14, 18C, 19F, or 23F is produced. In a particular embodiment, step (e) removes at least 98% of protein from the salt free retentate of step (d). In another embodiment, step (g) removes at least 90% of the protein from the clarified polysaccharide solution of step (f). In another embodiment, the diafiltration of step (h) comprises a pH adjustment to between about 5.5 to about 7.5. For improved stability of the substantially purified capsular polysaccharide during long-term storage, however, the diafiltration of step (h) comprises a pH adjustment to between about 7.0 to about 7.5, and more particularly to about 7.4.

The present invention also relates to a process for producing a solution containing substantially purified capsular polysaccharides from a *Streptococcus pneumoniae* cell lysate comprising serotype 19A comprising the steps of (a) providing a fermentation broth comprising bacterial cells that produce *Streptococcus pneumoniae* serotype 19A;

(b) lysing the bacterial cells in step (a) with a detergent, thereby producing a cell lysate comprising cell debris, soluble proteins, nucleic acids, and polysaccharides;

(c) clarifying the cell lysate of step (b) using centrifugation or filtration to remove cell debris, thereby producing a clarified cell lysate;

(d) ultrafiltering and diafiltering the clarified cell lysate of step (c) at about 4° C. at a pH of about 6 in sodium phosphate buffer, 25 mM sodium phosphate, to remove low molecular weight impurities and increase polysaccharide concentration, thereby producing a retentate;

(e) lowering the pH of the retentate of step (d) to less than 4.5, particularly about 3.5, to precipitate protein and nucleic acids, thereby forming an acidified retentate solution;

(f) holding the acidified retentate solution formed in step (e) for at least 2 hours at about 4° C. with or without agitation to allow settling of the precipitate, followed by filtration or centrifugation of the acidified retentate solution, thereby producing a clarified polysaccharide solution;

(g) adjusting the pH of the clarified polysaccharide solution of step (f) to about 6, thereby producing a pH-adjusted clarified polysaccharide solution;

(h) filtering the pH-adjusted clarified polysaccharide solution of step (g) through an activated carbon filter, particularly an activated carbon filter comprising wood-based phosphoric acid-activated carbon;

(i) ultrafiltering and diafiltering the filtered solution produced by step (h), thereby producing a concentrated purified polysaccharide solution; and (j) filtering the concentrated purified polysaccharide solution produced by step (i) using a sterile filter;

whereby a solution containing substantially purified capsular polysaccharides comprising serotype 19A is produced. In a particular embodiment, step (e) removes at least 98% of protein from the retentate of step (d). In another embodiment, step (h) removes at least 90% of the protein from the pH-adjusted clarified polysaccharide solution of step (g). In another embodiment, the diafiltration of step (i) comprises a pH adjustment to between about 5.5 to about 7.5. For improved stability of the substantially purified 19A polysaccharide during long-term storage, however, the diafiltration of step (i) comprises a pH adjustment to between about 7.0 to about 7.5, and more particularly to about 7.4.

The following examples are offered by way of illustration and not by way of limitation.

EXPERIMENTAL

The following Examples present results for *S. pneumoniae* polysaccharide serotypes 1, 4, 5, 6A, 6B, 7F, 9V, 14, 18C, 19A, and 19F purified at 10 L scale using the improved process of the present invention, and results are compared with those of the current purification process.

Example 1

Shortened Purification Process for *S. pneumoniae* Polysaccharide Serotypes 1, 4, 5, 6A, 6B, 7F, 14 and 19A

*S. pneumoniae* fermentation broths lysed with deoxycholate sodium (DOC) were obtained either within two days following their harvest or stored in 4° C. and processed within the following week. As described below, the present purification process included the following changes compared to the existing purification process: 1) the acidification step was moved from the beginning to after the first ultrafiltration/diafiltration (UF/DF) step, and the pH was adjusted to 3.5 instead of 5; 2) the diafiltration buffer was changed from 0.025 M phosphate to de-ionized (DI) water; 3) carbon adsorption was changed to 2 CUNO R32SP carbon disks (CUNO Inc., Wayne, N.J.) using wood-based phosphoric acid-activated carbon, and the adsorption time was extended from 4 to 12 turnovers (each turnover was 22 minutes); and 4) pH was adjusted to 7.4 during the last 30K diafiltration step when diafiltered about 5 times. The same purification procedure was applied to serotypes 1, 4, 5, 6A, 6B, or 7F. For serotype 19A, the steps were modified further and the purification was conducted in a chill room, as described below.

Purification Steps

All steps were conducted at room temperature except for type 19A, in which case the process was conducted at 4° C. in a chill room.

Clarification of the lysate: The purpose of this step was to remove cell debris and clarify the broth. This was accomplished either by centrifugation or filtration. The broth was centrifuged at 10,000 g for 30 min or until the broth was clear at 20° C. (4° C. for type 19A), or filtered with a Millipore Prefilter (Millipore Corp.,Billerica, Mass.) with the addition of CELPURE® filter aids (Advanced Minerals, Santa Barbara, Calif.). The clarified lysate was collected for further processing and the pellets were discarded.

First UF/DF (Ultrafiltration/Diafiltration): This step provided volume reduction and buffer exchange and also removed low molecular weight impurities. The clarified lysate was concentrated to about ⅛$^{th}$ original volume. Diafiltration was performed using about 10 volumes DI water (pH 6, 25 mM phosphate for 19A).

Acidification: More than 98% of the proteins were removed in this step. While stirring, concentrated phosphoric acid was added carefully to the retentate. The pH of the retentate was adjusted to a target value of pH 3.5. The acidified retentate was stirred for half an hour and aged in room temperature to age overnight (2 hours at 4° C. for 19A), resulting in the precipitation of protein and nucleic acids.

Clarification of Acidified Retentate: This was the clarification step to remove the precipitates after acidification. The slurry of acidified solution was centrifuged in a rotor at 10,000 rpm (17,000 Relative Centrifugal Force or RCF) for one hour at 20° C. (except for 6B, in which case the centrifugation was 6 hours at 37° C). The supernatant was collected and the pellet was discarded. Depth filtration with a Millipore Prefilter (Millipore Corp., Billerica, Mass.) with the addition of CELPURE®, filter aids (Advanced Minerals, Santa Barbara, Calif.) can also be used for this step.

Carbon Adsorption: In most cases, there was a slight yellow color after centrifugation of the acidified 100K retentate. The color removal was achieved by the carbon adsorption using wood-based phosphoric acid-activated carbon. This step also removed residual protein that remained after acidification. The clarified polysaccharide solution was recirculated through the carbon filter for 5-6 hours or overnight (for 19A, the pH was adjusted to 6 before carbon adsorption).

Final 30K UF/DF: This was another concentration and buffer exchange step to concentrate the solution to a final polysaccharide (PS) concentration of >2 g/L, which was diafiltered into deionized (DI) water. The carbon-filtered PS solution was concentrated. Then the concentrate was dialfiltered 10× with DI water. The pH was adjusted to 7.4 during the diafiltration.

Final 0.2 µm Sterile Filtration: The final PS solution was sterile filtered with a 0.22 µm filter or sterile disposable filter unit and stored in a 4° C. refrigerator.

Analytical Methods

Quantification of protein, PS, and nucleic acid concentrations were carried out using methods that are well known in the art, including SDS-PAGE (Sodium Dodecyl Sulfate Polyacrylamide Gel Electrophoresis) analysis, HPLC (High Performance Liquid Chromatography) and SEC (Size Exclusion Chromatography), modified Lowry assays, spectophotometry, SEC-MALLS (Size-Exclusion Chromatography/Multi-Angle Laser Light Scattering), and NMR (Nuclear Magnetic Resonance).

Results and Discussion

Type 5 Shortened Purification Batches: The comparison of final PS yield, PS molecular weight and major impurity levels of three purification batches using the shortened process and those using the current process for Type 5 are shown in Table 1. All the starting broths were DOC lysed high cell density fermentation batches, which had a higher polysaccharide concentration (~0.5 g/L) than the standard SOP fermentation broth (0.3 g/L). A 30K or 50K membrane was used for the first UF/DF step. The impurity levels were calculated using impurity/PS ratios. The same approach was used for all other serotypes described herein.

TABLE 1

Testing Data for Type 5 Shortened Purification Process Batches.

| BATCH # | PS YIELD (%) | PROTEIN RATIO (%) | NA RATIO (%) | PS MOLECULAR WEIGHT (KG/MOL) | C-PS RATIO (%) |
|---|---|---|---|---|---|
| L29276-27 (30K UF/DF) | 56.7 | 1.2 | 0.12 | 299 | 20.7 |
| L29276-32 (30K UF/DF) | 54.6 | 1.8 | 0.12 | 282 | 24.7 |
| L29276-52 (50KUF/DF) | 60.2 | 1.4 | 0.03 | 275 | 22.8 |
| Current process | 57 | 3.6 | 0.18 | 320 | 15.9 |
| Specification or expected value | 50-60 | ≤7.5 | ≤2.0 | NA | ≤35 |

As the data in Table 1 show, the protein ratios of all three batches using the shortened purification process met the specification of ≤7.5%, and were also comparable to that of the current process. The nucleic acid (NA) as well as C-polysaccharide (C-PS) ratios were also well below the specifications of ≤2.0% and ≤35%, respectively and were comparable to that of the current process. The results of the final PS yield and impurity levels of the three batches shown in Table 1 demonstrate the reproducibility and robustness of the shortened process.

There was some concern about whether polysaccharides could be hydrolyzed at a lower pH of 3.5. PS retention time change during the purification process was therefore monitored, and the molecular weight of the final purified PS was measured. No significant changes in serotype 5 PS retention time from the HPLC chromatogram were observed. There were also no significant differences in molecular weights for the purified PS by the shortened process and that of the current process (284 kg/mol) based on the MALLS measurement. Thus it was concluded that the molecular weight of purified PS was not adversely affected by the shortened purification process.

The in-process polysaccharide yield, protein/polysaccharide ratio and nucleic acid/polysaccharide ratio at each of the processing steps for the three shortened process batches are summarized in Table 2.

Table 2 shows that the activated carbon adsorption step also reduces protein/PS and NA/PS level. The percentage reduction was not as significant as the first two steps, but this step was important for removing the color of the solution and ensured that the impurity level met the specification.

Type 4 Shortened Purification Batches: A summary of three shortened purification batches for Type 4 is shown in Table 3. The feed broths for all three batches were DOC-lysed.

TABLE 2

Type 5 In-Process PS yield, Protein (SDS-PAGE) and Nucleic Acid Ratios.

| | PS YIELD (%) | | | PROTEIN/PS (%) | | |
|---|---|---|---|---|---|---|
| STEP | L29276-27 | L29276-32 | L29276-52 | L29276-27 | L29276-32 | L29276-52 |
| Broth | 100.0 | 100.0 | 100.0 | 384.40 | 1026.60 | 193.26 |
| Centrifugation | 99.9 | 95.6 | 94.6 | 274.60 | 642.00 | 209.78 |
| 30/50K UF/DF | 71.1 | 82.8 | 93.9 | 152.10 | 561.00 | 204.76 |
| Acidification | 56.1 | 65.9 | 58.6 | 9.00 | 7.50 | 0.20 |
| Carbon | 57.7 | 55.7 | 58.7 | 0.20 | 1.90 | 0.50 |
| 30K UF/DF | 54.5 | 54.6 | 60.3 | 0.10 | 1.00 | 0.09 |

| | NUCLEIC ACID/PS (%) | | |
|---|---|---|---|
| STEP | L29276-27 | L29276-32 | L29276-52 |
| Broth | 825.80 | 579.83 | 344.70 |
| Centrifugation | 505.10 | 484.30 | 311.90 |
| 30/50K UF/DF | 107.30 | 139.90 | 137.60 |
| Acidification | 9.44 | 16.40 | 7.38 |
| Carbon | 0.22 | 0.30 | 0.74 |
| 30K UF/DF | 0.11 | 0.12 | 0.19 |

There is always a loss of product during each step of any purification process. For these three shortened process batches, PS loss occurred mostly in the first UF/DF step and the acidification step. The loss of PS at the first UF/DF step was due to adsorption of PS or PS-protein complex to the surface of the membrane. This loss was minimized by rinsing the retentate side of the membrane with DI water after the diafiltration and combining the rinse with the original retentate. The loss of PS at the acidification step could be due to two reasons: physical adsorption of PS to the precipitation solids, and polysaccharide binding to the protein with co-precipitation during acidification. This second possibility was further investigated and results showed evidence of PS/protein binding.

FIG. 1 shows the reduction of protein/PS ratio at each purification step. Although the centrifugation step removed a small percentage of proteins, the majority of protein was removed at the acidification step. Only a trace amount of protein was detected after pH 3.5 treatment even for the highest protein potency batch.

Similar to protein/PS ratio, the nucleic acid/PS ratio showed variability of impurity levels among batches. The 30/50K UF/DF step removed a significant amount of nucleic acid as compared to protein removal in the same processing step. Without being bound by theory, this may have been due to the molecular size of nucleic acids being smaller than that of proteins, making them relatively easier to be removed via the 30/50K UF/DF step. The first centrifugation and acidification step also removed a considerable amount of nucleic acid.

TABLE 3

Type 4 Shortened Purification Batches Summary.

| BATCH | PS YIELD (%) | PROTEIN/ PS (%) | NUCLEIC ACID/PS (%) | PS MOLECULAR WEIGHT (KG/MOL) | C-PS RATIO (%) |
|---|---|---|---|---|---|
| L29276-47 | 56.3 | 0.7 | 0.04 | 289 | 15.4 |
| L29276-55 | 53.0 | 1.3 | 0.03 | 354 | 14.7 |
| L29276-148 | 57.3 | 1.16 | 0.02 | 293 | 10.0 |
| Current process | 71.1 | 0.05 | 0.02 | 285 | |
| Specification | NA | <3.0 | <2.0 | >350 | <25 |

The type 4 PS yield was also between 50-60%. Protein/PS ratio and nucleic acid/PS ratio were well within their specifications. C-PS ratio was also well within the specification. The molecular weight of all of the three batches were close to 300 kg/mol. Serotype 4 PS purified by the current purification process using the similar fermentation broth also gave a lower molecular weight 285 kg/mol. Comparison of the HPLC chromatographs of the PS from fermentation broth and the final purified solution showed that there were no differences in the PS retention time. This suggested that the difference in molecular weight difference was not caused by the process change, but rather due to intrinsic nature of the fermentation process.

Figure 2A:
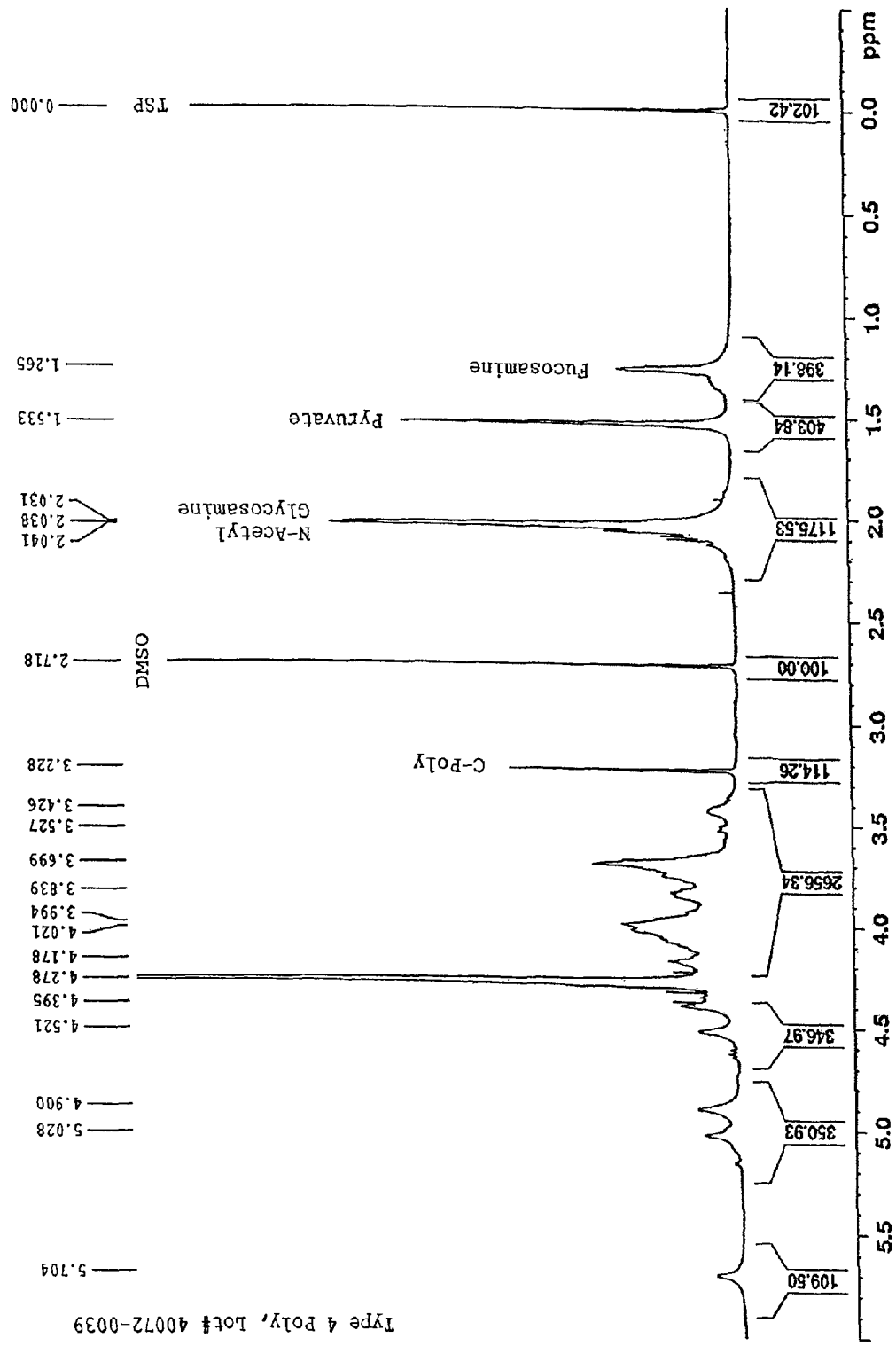
FIGS. 2A and 2B show NMR spectra for serotype 4 PS from the current purification process (A) compared to serotype 4 PS from the shortened purification process (B). No significant differences between the two spectra were observed. The second peak from the right in both spectra was pyruvate, and the pyruvate group peak height was comparable in both spectra.
Figure 2B:
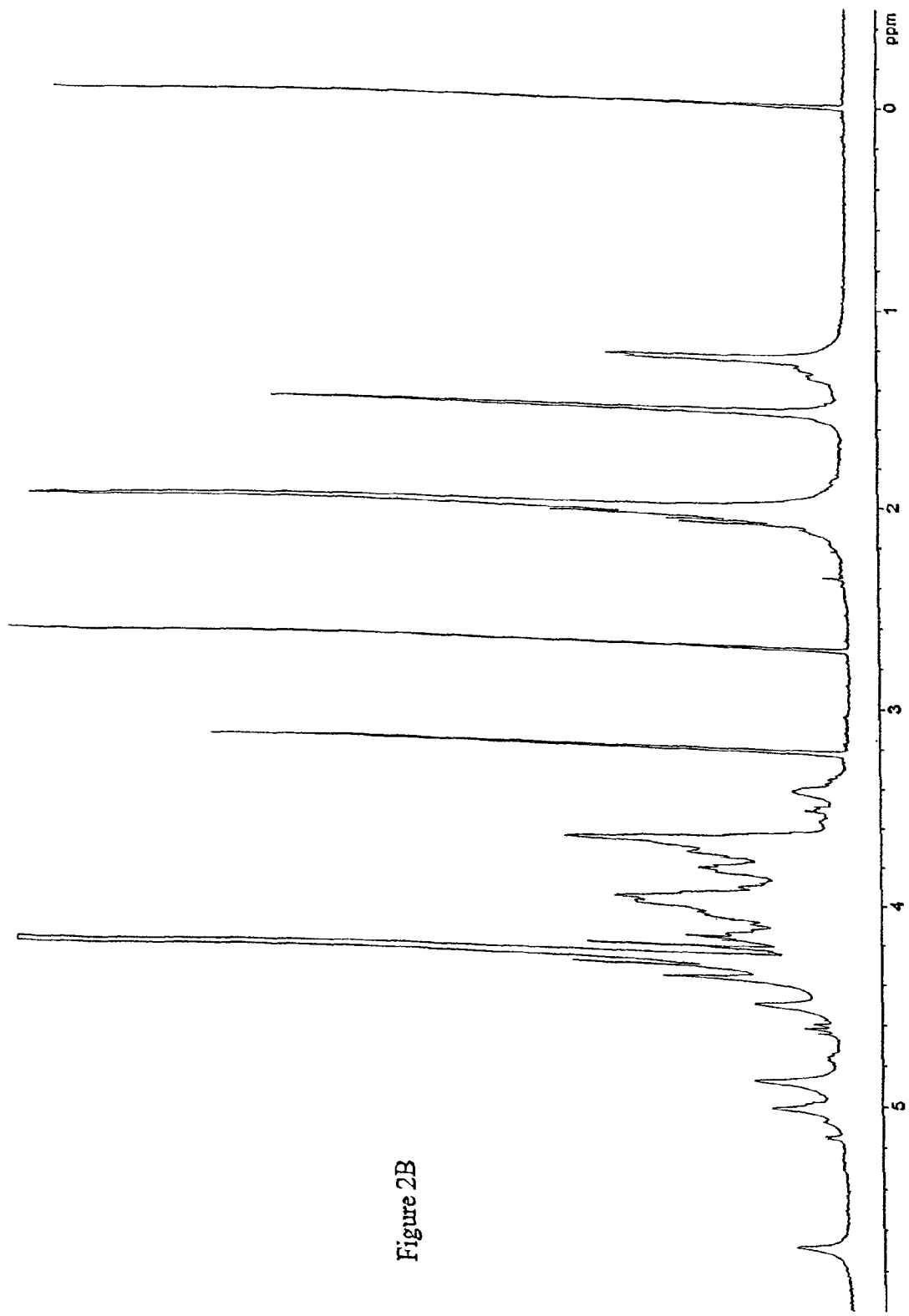

The Type 4 PS contains a pyruvate group in the purified molecule, and this pyruvate was important for conjugation for use in a pneumococcal conjugate vaccine. To ensure that the pyruvate amount was not adversely affected by acid treatment, NMR analysis was conducted. FIG. 2 shows the NMR spectra for standard type 4 PS and that from batch L29276-47. No significant differences between the two spectra were observed. The second peak from the right in both spectra was pyruvate, and the pyruvate group peak height was comparable in both spectra. The pyruvate ratios for all three shortened process batches were 0.8 mol/mol, and met the specification of >0.7 mol/mol.

The in-process PS yield, protein/PS and NA/PS ratio for the three type 4 batches are summarized in Table 4. PS loss occurred mostly at the first centrifugation, acidification and activated carbon adsorption steps, with an average of 10%, 8% and 20%, respectively. The overall PS yield was close to that of type 5, around 55%.

TABLE 4

Type 4 In-Process PS Yield, Protein (SDS-PAGE)/PS Ratio, and NA/PS Ratio.

| | PS YIELD (%) | | | PROTEIN/PS (%) | | |
|---|---|---|---|---|---|---|
| STEP | L29276-47 | L29276-55 | L29276-148 | L29276-47 | L29276-55 | L29276-148 |
| Broth | 100.0 | 100.0 | 100.0 | 231.22 | 297.33 | 499.75 |
| Centrifugation | 85.8 | 97.8 | 88.0 | 198.69 | 247.40 | 534.61 |
| 50/100K UF/DF | 85.1 | 86.4 | 87.7 | 235.90 | 249.24 | 364.98 |
| Acidification | 84.2 | 72.0 | 78.6 | 0.42 | 1.81 | 0.41 |
| Carbon | 65.3 | 48.9 | 58.6 | 0.09 | 0.39 | 0.34 |
| 30K UF/DF | 57.9 | 50.6 | 57.4 | 0.08 | 0.09 | 1.31 |

| | NA/PS (%) | | |
|---|---|---|---|
| STEP | L29276-47 | L29276-55 | L29276-148 |
| Broth | 312.84 | 282.50 | 302.71 |
| Centrifugation | 301.40 | 261.82 | 243.28 |
| 50/100K UF/DF | 80.99 | 67.67 | 92.00 |
| Acidification | 4.24 | 5.01 | 1.17 |
| Carbon | 0.08 | 0.92 | 0.38 |
| 30K UF/DF | 0.05 | 0.06 | 0.07 |

Figure 3:
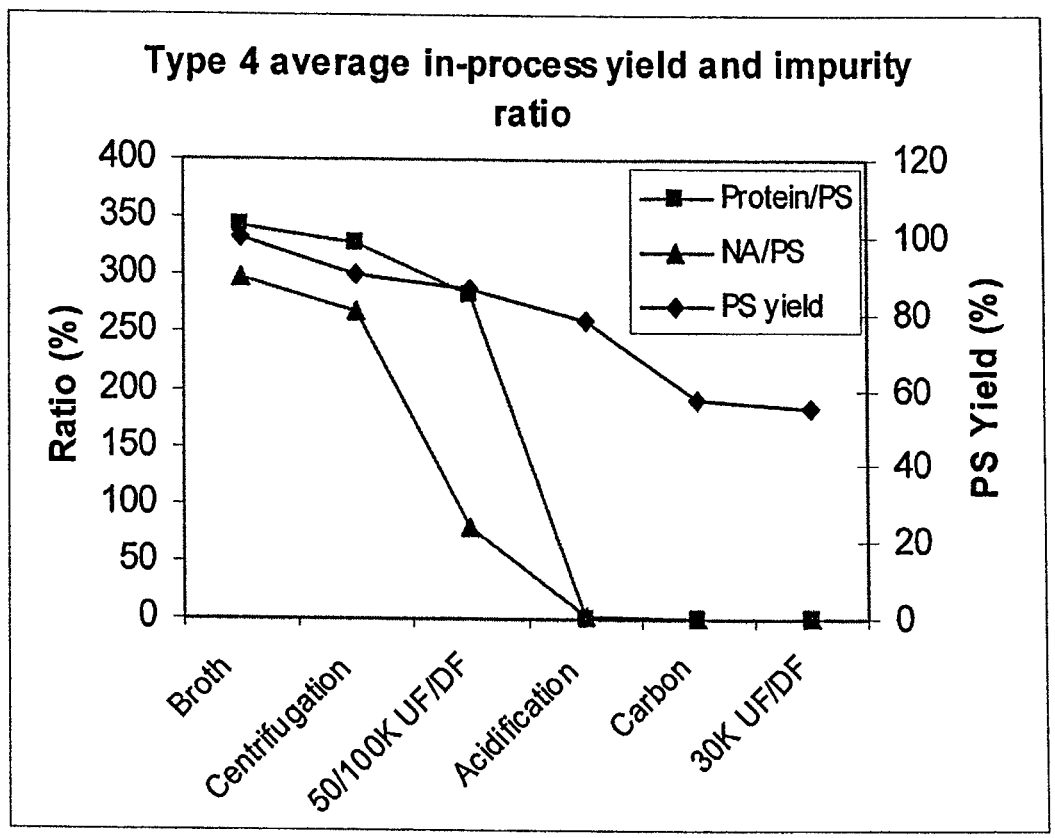
FIG. 3 shows average in-process PS yield, protein/PS ratio, and NA/PS ratio for serotype 4 using the shortened purification process of the invention. Results are shown for each purification step.

FIG. 3 shows average PS yield, protein/PS and NA/PS ratio change at each of the purification steps for the three batches in Table 4. The protein removal occurred mostly at the acidification step as expected. The first centrifugation and UF/DF steps also collectively removed a certain amount of protein, but the protein reduction was less than the acidification step.

Similar to type 5, the most nucleic acid/PS ratio reduction took place at the 50/100K UF/DF, first centrifugation, and the acidification steps, and the NA reduction at the first UF/DF step was more significant than that for proteins. Again, as shown in FIG. 3, the activated carbon step removed a certain amount of protein and NA and brought the impurity levels below the specifications. It also removed the color of the solution as well.

Type 19A Shortened Purification Batches: Type 19A polysaccharide is unstable and the molecular weight changes during purification. The shortened purification process was modified slightly in order to stabilize the 19A polysaccharide. These modifications are summarized as follows: 1) the purification steps were mostly conducted at 4° C. in the chill room; 2) the first 100K diafiltration was chilled using 25 mM phosphate buffer (4° C.) with a pH of 6 instead of using room temperature water; 3) the acidification holding time was reduced from overnight to 2 hours; and 4) after clarifying the acidified 100K retentate, the pH was adjusted to 6 and activated carbon adsorption was conducted at pH 6 instead of 3.5.

The results of two 19A batches purified by the shortened purification process are shown in Table 5.

TABLE 5

Type 19A Shortened Purification Batches Summary.

| BATCH | PS YIELD (%) | PROTEIN/PS (%) | NA/PS (%) | MOLECULAR WEIGHT (KG/MOL) | C-PS (%) |
|---|---|---|---|---|---|
| L29276-116 | 61.58 | 0.14 | 0.01 | 525 | 3.8 |

TABLE 5-continued

Type 19A Shortened Purification Batches Summary.

| BATCH | PS YIELD (%) | PROTEIN/PS (%) | NA/PS (%) | MOLECULAR WEIGHT (KG/MOL) | C-PS (%) |
|---|---|---|---|---|---|
| L29276-143 | 76.15 | 1.43 | 0.01 | 488 | 2.8 |
| Specification | NA | <2 | <2 | NA | <10 |

The PS yields of the two shortened purification batches were 62 and 76% respectively. Final protein/PS ratio, nucleic acid ratio, and C-PS ratio all met their respective specifications. The final molecular weights of polysaccharides from the two batches were 525 kg/mol and 488 kg/mol, respectively, and were close to that of the PS of 19A used in phase III clinical trials (486 kg/mol).

The protein/PS ratio for the two batches both met the specification of <2%. Both NA and C-PS ratio of the two batches were well within their specifications.

Figure 4:
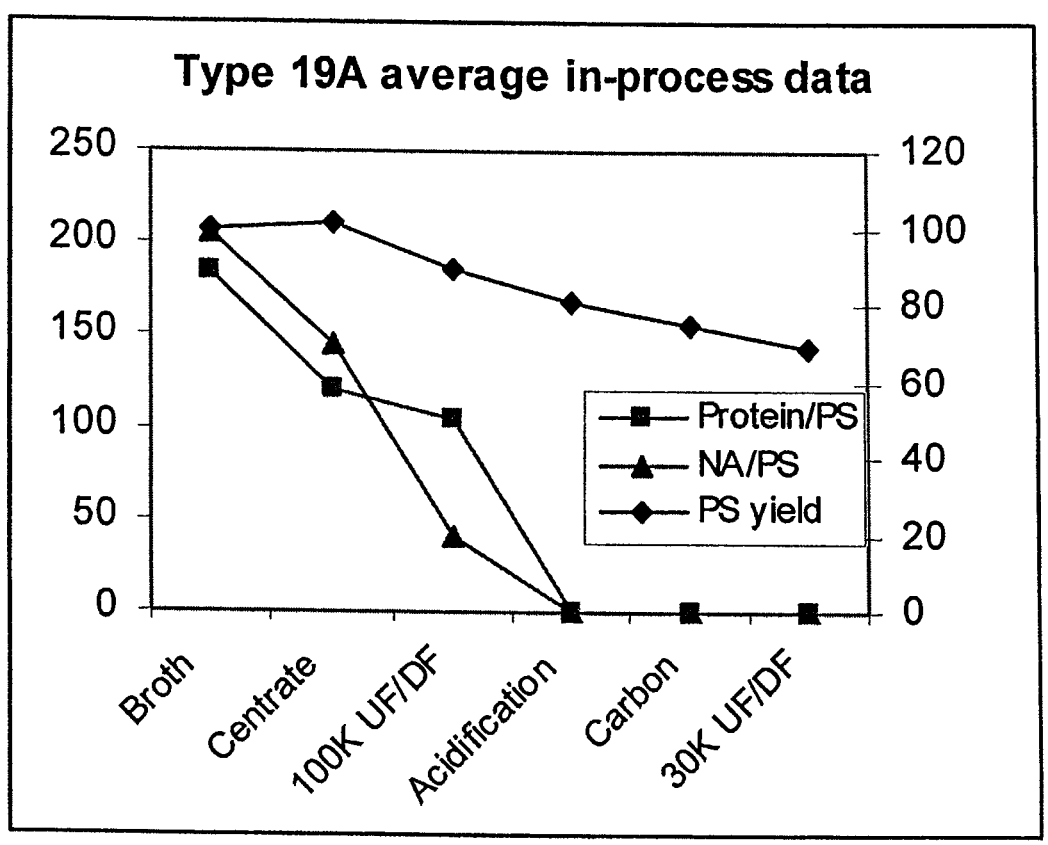
FIG. 4 shows average in-process PS yield, protein/PS ratio, and NA/PS ratio for serotype 19A using the shortened purification process of the invention. Results are shown for each purification step.

The PS yield, protein and NA reduction at each of the purification steps are shown in Table 6 and FIG. 4. The results showed PS loss at each of the purification steps except the first centrifugation step. Like serotypes 5 and 4, protein and NA removal mostly took place at the first three steps, and there was hardly any detectable protein and NA left after acidification. Although the activated carbon adsorption step did not remove a significant amount of protein and NA, possibly due to very low protein and NA concentration after the acidification, the step was still needed for color removal.

TABLE 6

Type 19A In-Process PS Yield, Protein/PS and NA/PS Ratio.

| | PS YIELD (%) | | PROTEIN/PS (%) | | NA/PS (%) | |
|---|---|---|---|---|---|---|
| STEP | L29276-116 | L29276-143 | L29276-116 | L29276-143 | L29276-116 | L29276-143 |
| Broth | 100.0 | 100.0 | 224.41 | 144.08 | 277.55 | 134.73 |
| Centrate | 100.8 | 101.2 | 121.60 | 119.11 | 189.64 | 100.64 |
| 100K UF/DF | 87.7 | 90.3 | 103.83 | 105.16 | 56.87 | 26.36 |
| Acidification | 90.4 | 72.1 | 0.28 | 0.84 | 0.03 | 0.03 |
| Carbon | 77.8 | 71.7 | 0.96 | 0.03 | 0.04 | 0.02 |
| 30K UF/DF | 61.0 | 76.1 | 0.54 | 0.00 | 0.02 | 0.01 |

Type 7F Shortened Purification Batches: Type 7F is a non-ionic polysaccharide, which typically requires change in steps during purification using the existing process compared to the serotypes described above). However, the shortened purification process of the present invention was successfully applied to serotype 7F without the need for process deviation. Two batches of type 7F broth were purified using the shortened process. One was a standard fermentation broth (L29276-107) and one was a high cell density broth (L29276-157). The results of the two batches are summarized in Table 7.

TABLE 7

Type 7F Shortened Purification Batches Summary.

| BATCH # | PS YIELD (%) | PROTEIN/PS (%) | NA/PS (%) | MOLECULAR WEIGHT (KG/MOL) | C-PS (%) |
|---|---|---|---|---|---|
| L29276-107 | 65.27 | 0.49 | 0.02 | 968 | 3.3 |
| L29276-157 | 79.06 | 0.26 | 0.04 | 881 | 2.9 |
| Specification | NA | <5 | <2 | NA | <17 |

The PS yield of type 7F was actually higher than the other serotypes, possibly due to less binding of the non-ionic polymer to the charged protein molecules. Final protein, NA and C-PS ratios were all well within their specifications. Molecular weight of type 7F was comparable to that of standard batches and even though the 7F molecular weight was quite high, the PS solution was not very viscous due to smaller excluded volume of the nonionic polymer.

Figure 5:
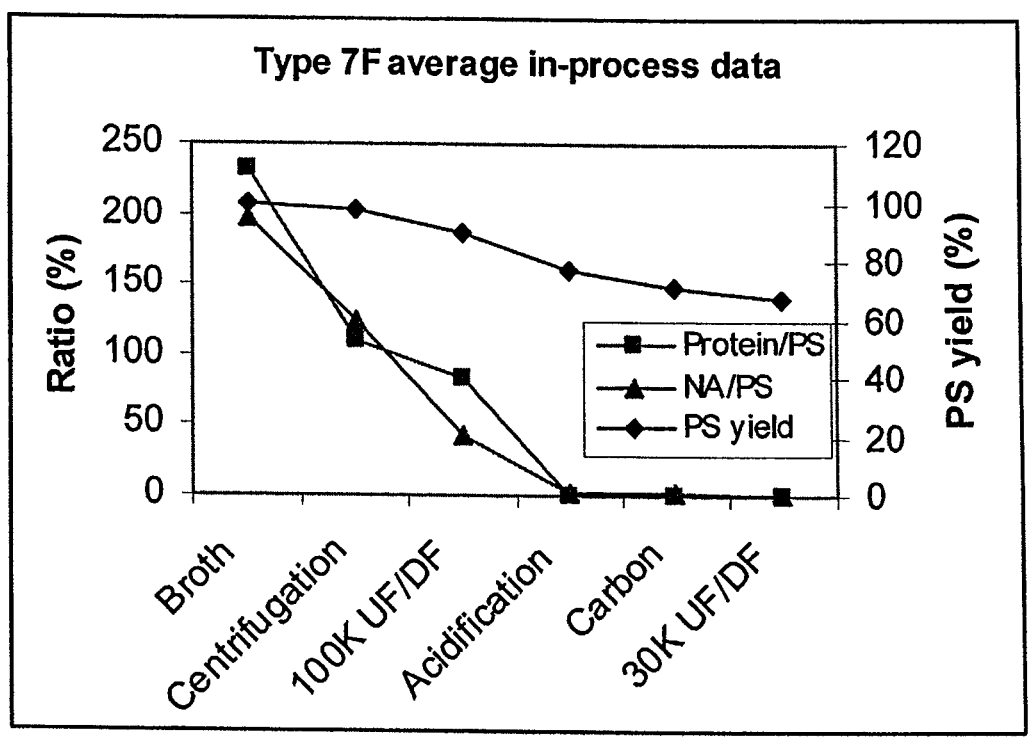
FIG. 5 shows average in-process PS yield, protein/PS ratio, and NA/PS ratio for serotype 7F using the shortened purification process of the invention. Results are shown for each purification step.

Type 7F PS yield, protein and NA ratio at each of the purification steps are shown in Table 8 and the average of the two batches was plotted in FIG. 5.

TABLE 8

Type 7F In-Process PS Yield, Protein/PS, and NA/PS Ratio.

| | PS YIELD (%) | | PROTEIN/PS (%) | | NUCLEIC ACID/PS (%) | |
|---|---|---|---|---|---|---|
| STEP | L29276-107 | L29276-157 | L29276-107 | L29276-157 | L29276-107 | L29276-157 |
| Broth | 100.00 | 100.00 | 274.10 | 189.24 | 258.55 | 134.64 |
| Centrifugation | 100.31 | 95.57 | 110.60 | 107.20 | 163.38 | 83.14 |
| 100K UF/DF | 84.19 | 95.39 | 139.38 | 27.53 | 54.02 | 32.74 |
| Acidification | 70.89 | 84.08 | 0.44 | 0.10 | 1.80 | 0.94 |
| Carbon | 63.96 | 79.40 | 0.70 | 0.09 | 2.29 | 0.23 |
| 30K UF/DF | 57.24 | 77.70 | 0.30 | 0.05 | 0.06 | 0.00 |

There was some Type 7F PS loss at each purification step. Overall, PS loss was less than that of serotypes 5 and 4. Protein and NA ratio reduction was mostly by the first centrifugation, 100K UF/DF, and acidification steps. Similar to other serotypes, the 100K UF/DF was more efficient in removing NA than proteins. Although the activated carbon adsorption step did not remove a significant amount of protein and NA due to very low impurity levels after acidification, the step was still needed for color removal.

Type 6B Shortened Purification Batches: Two batches of 6B were purified using the shortened purification process. It was found the clarification of the acidified 100K retentate took a longer time than the other serotypes (6 hours instead of 1 hour). Except for this difference, the purification process was similar to that of the serotypes. The results of the two batches are summarized in Table 9.

TABLE 9

Type 6B Shortened Purification Summary.

| BATCH | PS YIELD (%) | PROTEIN/PS (%) | NA/PS (%) | MOLECULAR WEIGHT (KG/MOL) | C-PS (%) |
|---|---|---|---|---|---|
| L29276-161 | 69.50 | 1.73 | 0.28 | 857 | 3.6 |
| L29276-164 | 74.50 | 1.41 | 0.17 | 1142 | 3.9 |
| Specification | NA | <4 | <1 | >800 | <10 |

All impurity levels (protein, NA, and C-PS) were well within their specifications. The PS yield was relatively high, and so were the protein and NA ratio compared to the other serotypes.

Figure 6:
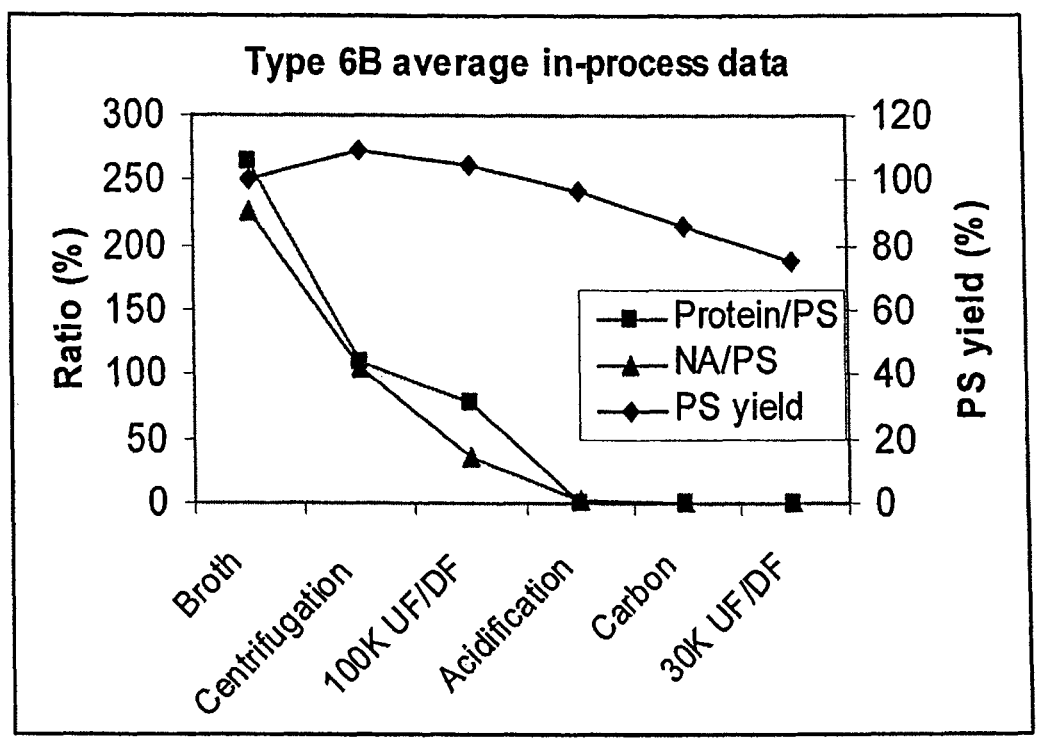
FIG. 6 shows average in-process PS yield, protein/PS ratio, and NA/PS ratio for serotype 6B using the shortened purification process of the invention. Results are shown for each purification step.

The in-process PS yield, protein and NA ratios at each of the purification steps are shown in Table 10 and FIG. 6.

TABLE 10

Type 6B Average In-Process PS Yield, Protein, and NA Ratio.

| STEP | PS YIELD (%) | | PROTEIN/PS (%) | | NUCLEIC ACID/PS (%) | |
|---|---|---|---|---|---|---|
| | L29276-161 | L29276-164 | L29276-161 | L29276-164 | L29276-161 | L29276-164 |
| Broth | 100.00 | 100.00 | 238.20 | 288.80 | 215.12 | 237.67 |
| Centrifugation | 101.43 | 116.54 | 95.88 | 123.59 | 104.08 | 104.47 |
| 100K UF/DF | 104.11 | 105.47 | 68.15 | 88.14 | 22.13 | 47.81 |
| Acidification | 91.98 | 101.45 | 0.71 | 0.43 | 1.06 | 2.24 |
| Carbon | 80.71 | 91.42 | 0.39 | 0.23 | 0.45 | 0.74 |
| 30K UF/DF | 72.67 | 77.28 | 1.23 | 0.46 | 0.37 | 0.25 |

Similar to 19A, PS loss occurred at each of the purification steps except the first centrifugation step, in which there was a slight increase of PS. Removal of protein and NA was achieved mostly by the first centrifugation, the first 100K UF/DF, and acidification steps. However, there was also some reduction of protein and NA ratio at the activated carbon adsorption step.

Type 6A Shortened Purification Batches: Two batches of type 6A were purified using the shortened purification process. The PS yield, impurity levels and molecular weight of the final solutions are summarized in Table 11.

TABLE 11

Type 6A Shortened Purification Batches Summary.

| BATCH | BROTH | PS YIELD (%) | PROTEIN/PS (%) | NA/PS (%) | MOLECULAR WEIGHT (KG/MOL) | C-PS (%) |
|---|---|---|---|---|---|---|
| L29276-138 | Standard | 75.75 | 1.23 | 0.04 | 640 | 7.3 |
| L29276-183 | High cell density | 72.56 | 0.20 | 0.01 | 670 | 5.1 |
| Specification | | NA | <2.00 | <2.00 | NA | <15 |

The final PS yields of the two 6A batches were both >70%, which were the highest among the serotypes processed using the shortened process. Protein, NA, and C-PS ratios were all within specifications.

were already below their specifications. For protein, the acidification was the most efficient step, while for NA, 100K UF/DF reduced the most NA/PS ratio. Although the activated carbon adsorption step did not remove a significant amount of protein and NA due to very low impurity levels after acidification, the step was still needed for color removal.

TABLE 12

Type 6A In-Process PS Yield, Protein and NA Ratio.

| STEP | PS YIELD (%) | | PROTEIN/PS (%) | | NUCLEIC ACID/PS (%) | |
|---|---|---|---|---|---|---|
| | L29276-138 | L29276-183 | L29276-138 | L29276-183 | L29276-138 | L29276-183 |
| Broth | 100.00 | 100.00 | 214.35 | 138.71 | 211.45 | 163.88 |
| Centrifugation | 99.35 | 97.80 | 183.43 | 149.71 | 177.03 | 150.41 |
| 100K UF/DF | 93.19 | 100.40 | 114.72 | 103.00 | 43.38 | 40.43 |
| Acidification | 89.87 | 87.90 | 0.16 | 0.87 | 1.09 | 0.97 |
| Carbon | 76.02 | 75.70 | 0.62 | 0.85 | 0.09 | 0.07 |
| 30K UF/DF | 75.57 | 72.90 | 0.00 | 0.07 | 0.04 | 0.02 |

Figure 7:
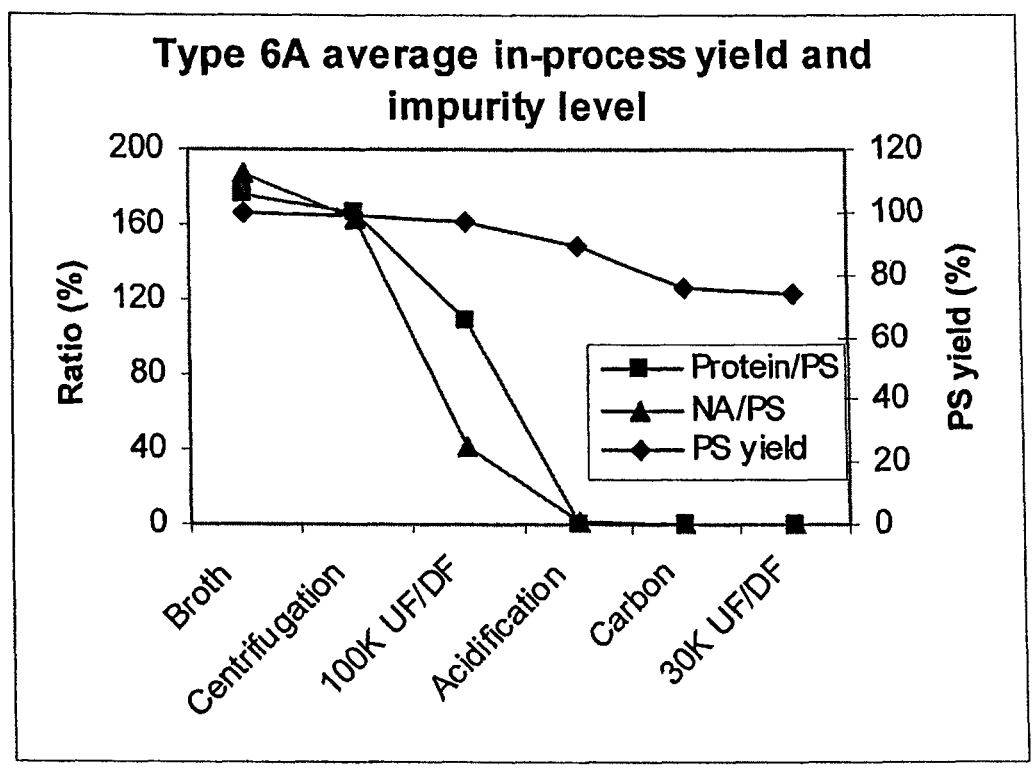
FIG. 7 shows average in-process PS yield, protein/PS ratio, and NA/PS ratio for serotype 6A using the shortened purification process of the invention. Results are shown for each purification step.

Table 12 and FIG. 7 show in-process PS yield, protein and NA ratio change at each of the purification steps. There was hardly any loss of PS at the first centrifugation and 100K UF/DF steps. About 10-15% PS loss occurred at the acidification and activated carbon adsorption steps, which was close to that of the other serotypes. The most protein and NA ratio reduction was by the first centrifugation, 100K UF/DF, and acidification. After acidification, both protein and NA ratios Type 1 Shortened Purification Batches: Two batches of type 1 purified by the shortened process are summarized in Table 13. Batch L29276-170 was purified from high cell density fermentation broth and L29276-173 was from standard fermentation broth.

TABLE 13

Type 1 Shortened Purification Batch Summary.

| BATCH | BROTH | PS YIELD (%) | PROTEIN/PS (%) | NA/PS (%) | MOLECULAR WEIGHT (KG/MOL) | C-PS (%) |
|---|---|---|---|---|---|---|
| L29276-170 | High cell density | 50.96 | 0.44 | 0.08 | 501 | 5.3 |
| L29276-173 | SOP | 53.84 | 1.23 | 0.01 | 458 | 11.9 |
| Specification | | NA | <2 | <2 | NA | <15 |

The PS yields of both batches were about 50%, and the impurity levels for protein, NA and C-PS were all within their specifications.

Figure 8:
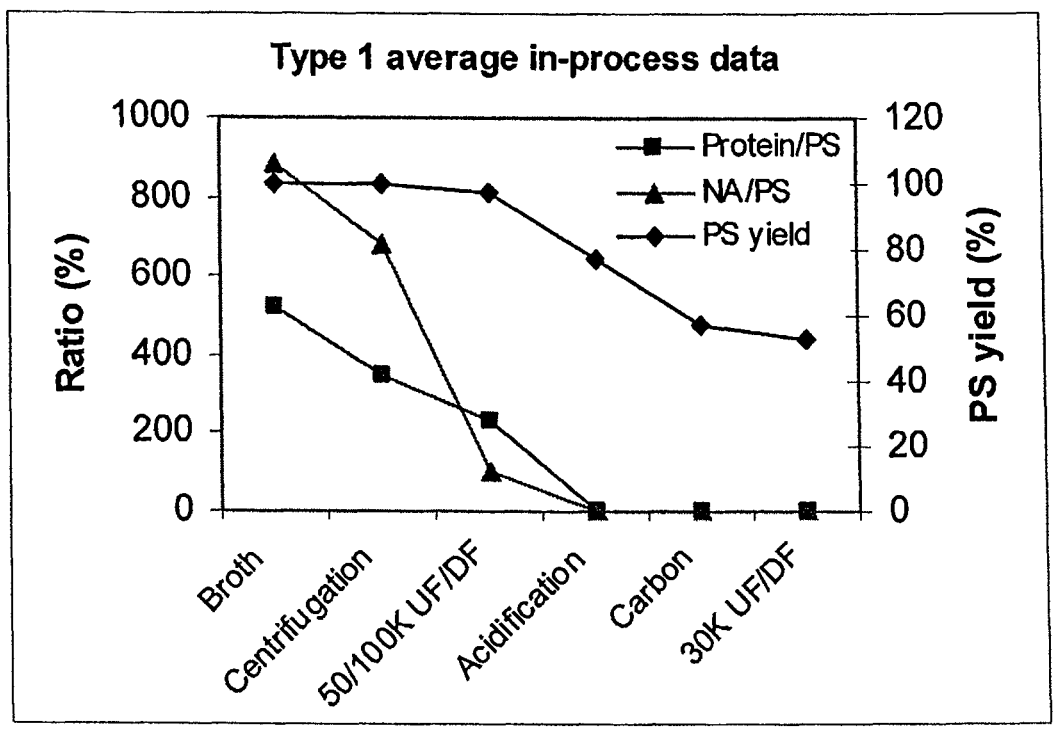
FIG. 8 shows average in-process PS yield, protein/PS ratio, and NA/PS ratio for serotype 1 using the shortened purification process of the invention. Results are shown for each purification step.

The in-process PS yield, protein and NA ratios after each of the purification steps are shown in Table 14 and FIG. 8. The trends were similar to other serotypes purified. PS loss occurred mostly at the acidification and activated carbon adsorption steps, and most of protein and NA removal occurred at the first three steps. More NA was removed at the 100K UF/DF step than proteins. Although the activated carbon adsorption step did not remove a significant amount of protein and NA due to very low impurity levels after acidification, the step was still needed for color removal.

TABLE 14

Type 1 Average In-Process PS Yield, Protein and NA Ratio.

| | PS YIELD (%) | | PROTEIN/PS (%) | | NA/PS (%) | |
|---|---|---|---|---|---|---|
| STEP | L29276-170 | L29276-173 | L29276-170 | L29276-173 | L29276-170 | L29276-173 |
| Broth | 100.00 | 100.00 | 453.30 | 595.20 | 594.41 | 1178.98 |
| Centrifugation | 93.99 | 105.63 | 301.86 | 396.97 | 340.55 | 1018.47 |
| 50/100K UF/DF | 88.33 | 105.62 | 232.34 | 235.08 | 17.49 | 182.56 |
| Acidification | 66.54 | 87.67 | 0.54 | 4.87 | 1.09 | 5.85 |
| Carbon | 55.85 | 59.69 | 1.91 | 1.86 | 0.49 | 0.01 |
| 30K UF/DF | 51.24 | 55.59 | 0.36 | 0.92 | 1.65 | 0.01 |

Type 14 Shortened Purification Batches: Two batches of serotype 14 were purified using the shortened purification process with no process deviations. The final PS yield, and impurity levels are summarized in Table 15.

TABLE 15

Type 14 Shortened Purification Batches Summary.

| BATCH | BROTH | PS YIELD (%) | PROTEIN/PS (%) | NA/PS (%) | MOLECULAR WEIGHT (KG/MOL) | C-PS (%) |
|---|---|---|---|---|---|---|
| L32874-155 | High cell density | 51.3 | 2.06 | 0.03 | 520 | 4.2 |
| L32874-163 | SOP | 56.7 | 1.39 | 0.03 | 662 | 2.9 |
| Specification | | NA | <3 | <2 | >400 | <15 |

Similar to serotype 7F, serotype 14 is a non-ionic polysaccharide, and its current purification process is slightly different from the other serotypes. However, the shortened purification process of the present invention was successfully applied to serotype 14 without the need for such additional steps. The PS yields of the two shortened purification process batches were 50-60%, and protein and NA ratios were within their specifications. The molecular weights of the purified PS also met the specification.

Figure 9:
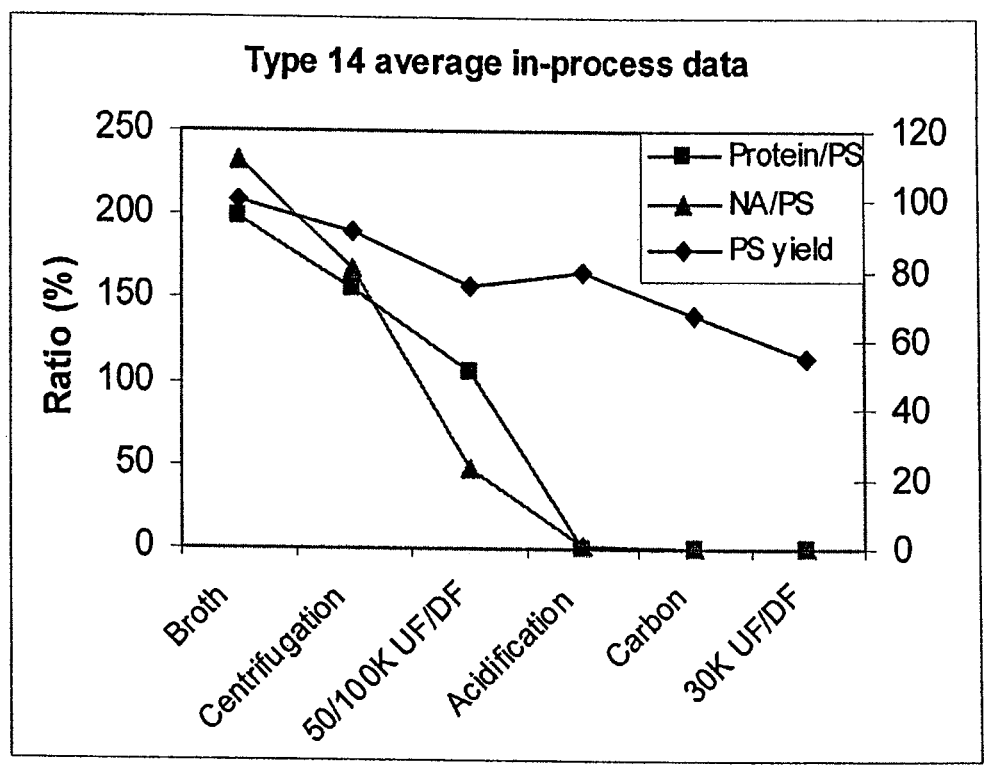
FIG. 9 shows average in-process PS yield, protein/PS ratio, and NA/PS ratio for serotype 14 using the shortened purification process of the invention. Results are shown for each purification step.

In-process PS yield, protein and NA ratios are summarized in Table 16 and FIG. 9. Similar trends of PS loss, protein and NA removal were observed as for the other tested serotypes described above.

TABLE 16

Type 14 Average In-Process PS Yield, Protein, and NA Ratio.

| STEP | PS YIELD (%) | | PROTEIN/PS (%) | | NA/PS (%) | |
|---|---|---|---|---|---|---|
| | L32874-155 | L232874-163 | L32874-155 | L232874-163 | L32874-155 | L232874-163 |
| Broth | 100.00 | 100.00 | 109.73 | 286.56 | 192.80 | 272.50 |
| Centrifugation | 91.40 | 90.80 | 110.88 | 201.48 | 135.50 | 201.82 |
| 50/100K UF/DF | 82.40 | 68.70 | 45.52 | 165.69 | 47.10 | 64.54 |
| Acidification | 65.40 | 93.90 | 0.65 | 0.47 | 0.89 | 1.08 |
| Carbon | 59.40 | 74.60 | 0.60 | 0.10 | 0.17 | 0.21 |
| 30K UF/DF | 53.10 | 57.60 | 0.57 | 0.41 | 0.13 | 0.25 |

Example 2

Comparison of Different Serotypes (Serotypes 1, 4, 5, 6A, 6B, 7F, 9V, 14, 18C, 19A, and 19F)

Figure 10:
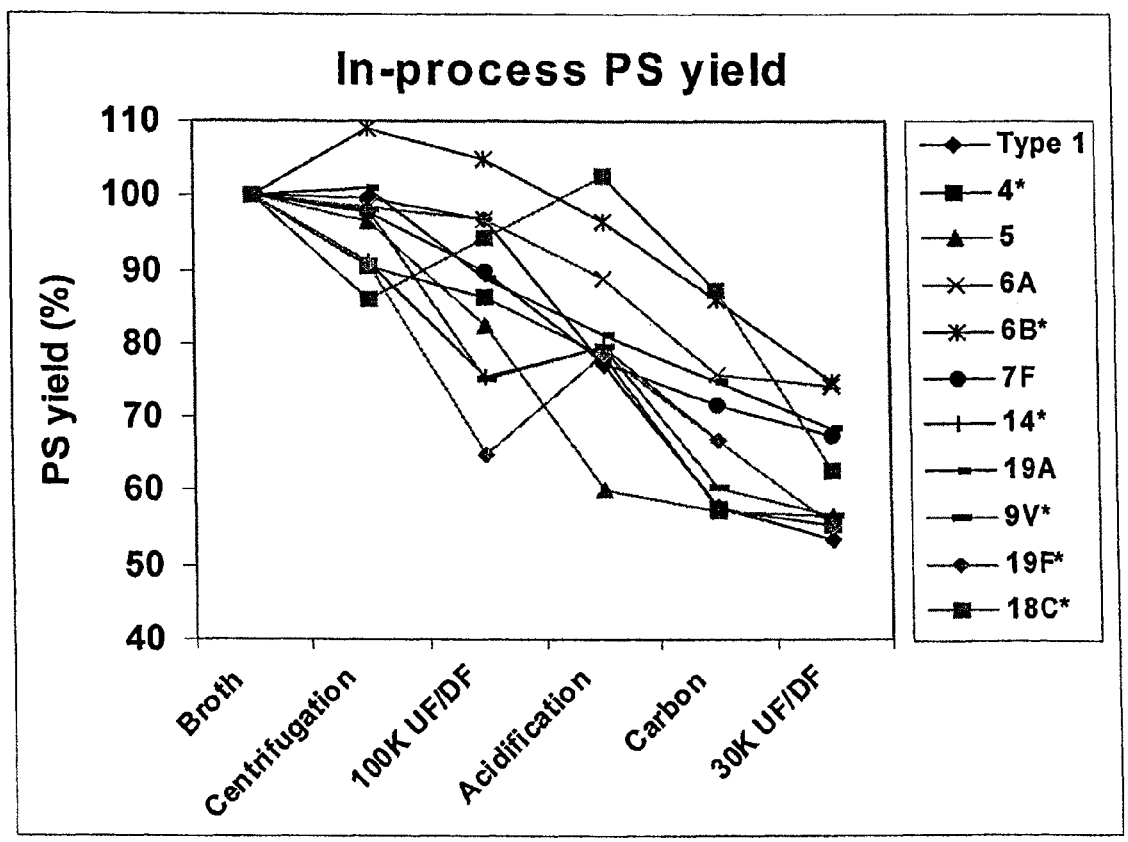
FIG. 10 shows a comparison of PS in-process yields for serotypes 1, 4, 5, 6A, 6B, 7F, 9V, 14, 18C, 19A, and 19F purified using the shortened purification process of the invention.

To compare purification of the different serotypes using the shortened purification process of the present invention, PS removal for all the serotypes described in Example 1 plus serotypes 9V, 18C, and 19F were plotted in one graph in FIG. 10. Most of the serotypes followed a similar trend with PS loss at each of the purification steps. There was an increase of PS yield for type 6B at the first centrifugation step and type 14 at the acidification step. PS percentage loss varied from serotype to serotype. Type 5 seemed to lose most PS at the acidification step and type 4 at the activated carbon adsorption step.

Figure 11:
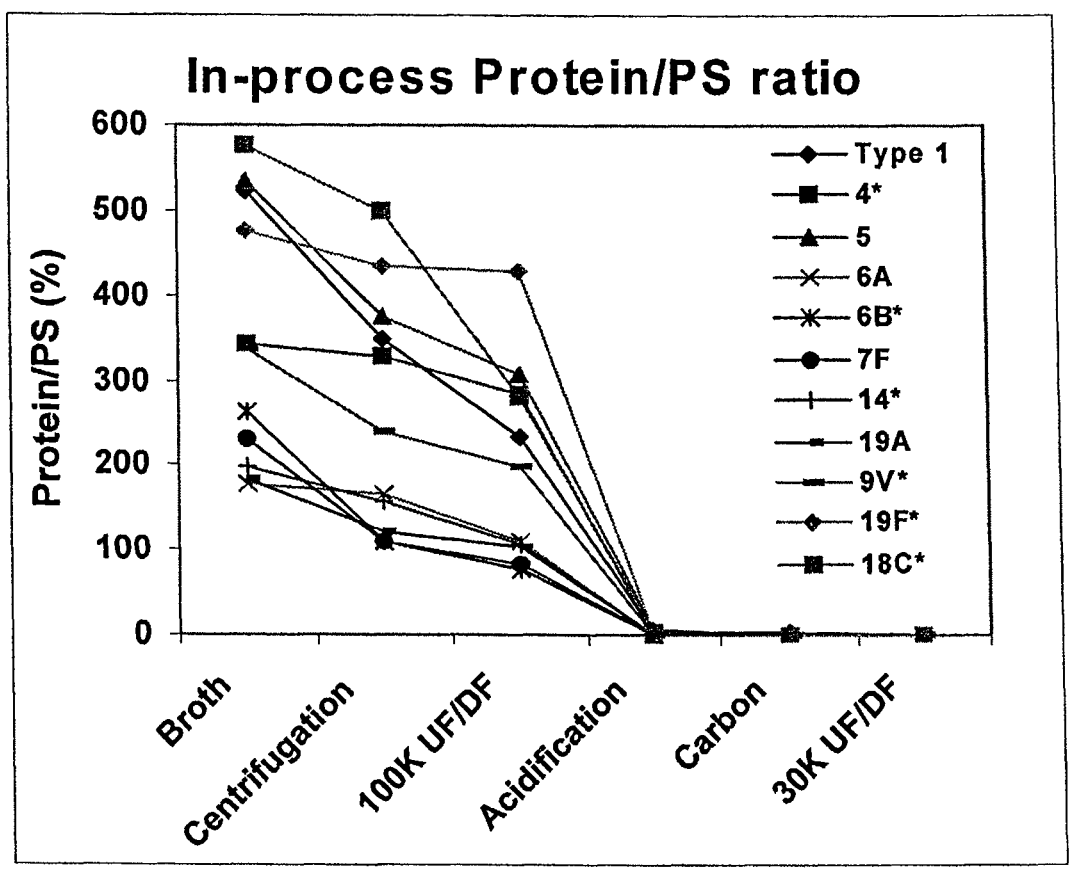
FIG. 11 shows a comparison of protein/PS ratios for serotypes 1, 4, 5, 6A, 6B, 7F, 9V, 14, 18C, 19A, and 19F purified using the shortened purification process of the invention. Results are compared for each purification step.

Protein/PS ratios for each purification step for each of the serotypes are shown in FIG. 11. The figure shows that there was a difference in initial protein/PS ratios for different serotypes, with types 1, 4, 5, 9V, 19F, and 18C having the highest initial protein/PS ratios. Even though the protein/PS ratios were much higher for types 1, 4, 5, 9V, 19F, and 18C compared to the other serotypes even after the first UF/DF step, the acidification step greatly reduced the protein/PS ratio and not much protein was left after this step.

Figure 12:
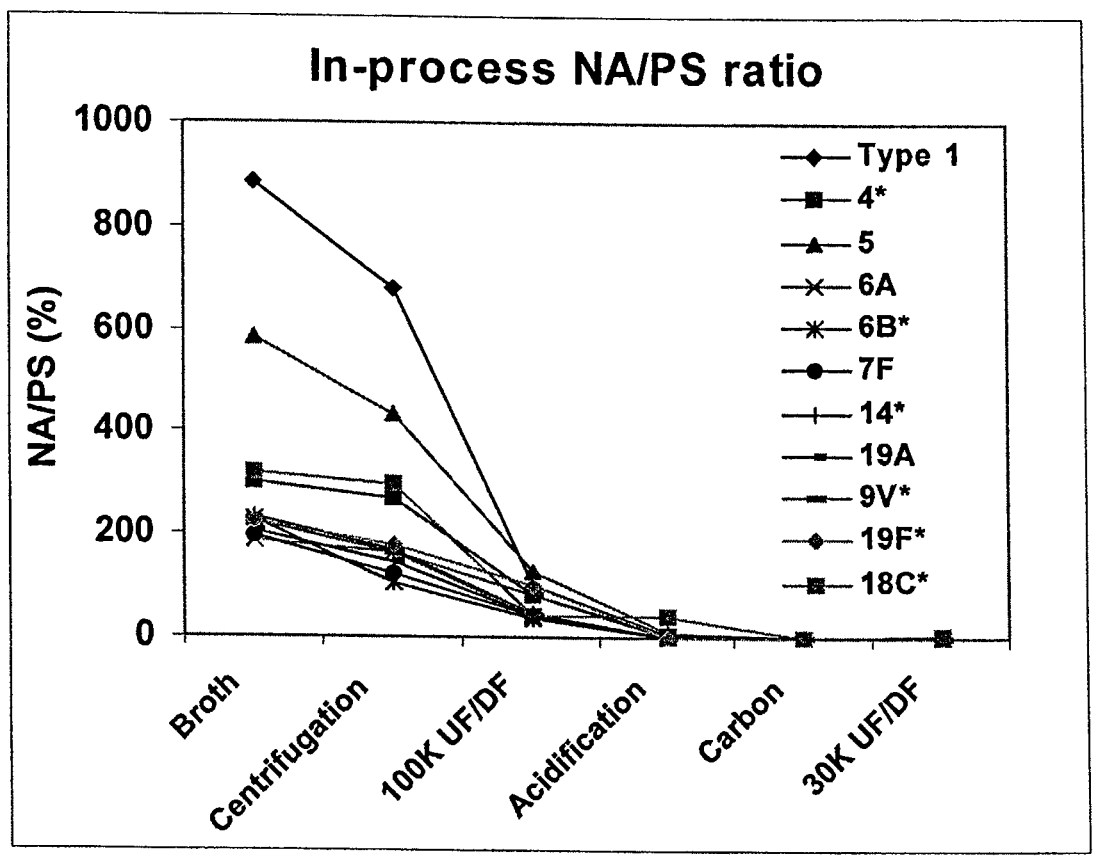
FIG. 12 shows a comparison of NA/PS ratios for serotypes 1, 4, 5, 6A, 6B, 7F, 9V, 14, 18C, 19A, and 19F purified using the shortened purification process of the invention. Results are compared for each purification step.

As shown in FIG. 12, NA/PS ratios also varied from serotype to serotype. Types 1 and 5 had the highest NA/PS ratio, followed by types 18C and 4. The first centrifugation and UF/DF step removed a significant amount of NA for these serotypes and type 1 seemed to be the most efficient. There was very little NA left after the acidification step.

Example 3

Acidification and Activated Carbon Adsorption Step Efficiency Analysis (Serotypes 1, 4, 5, 6A, 6B, 7F, 9V, 14, 18C, 19A, and 19F)

Figure 13:
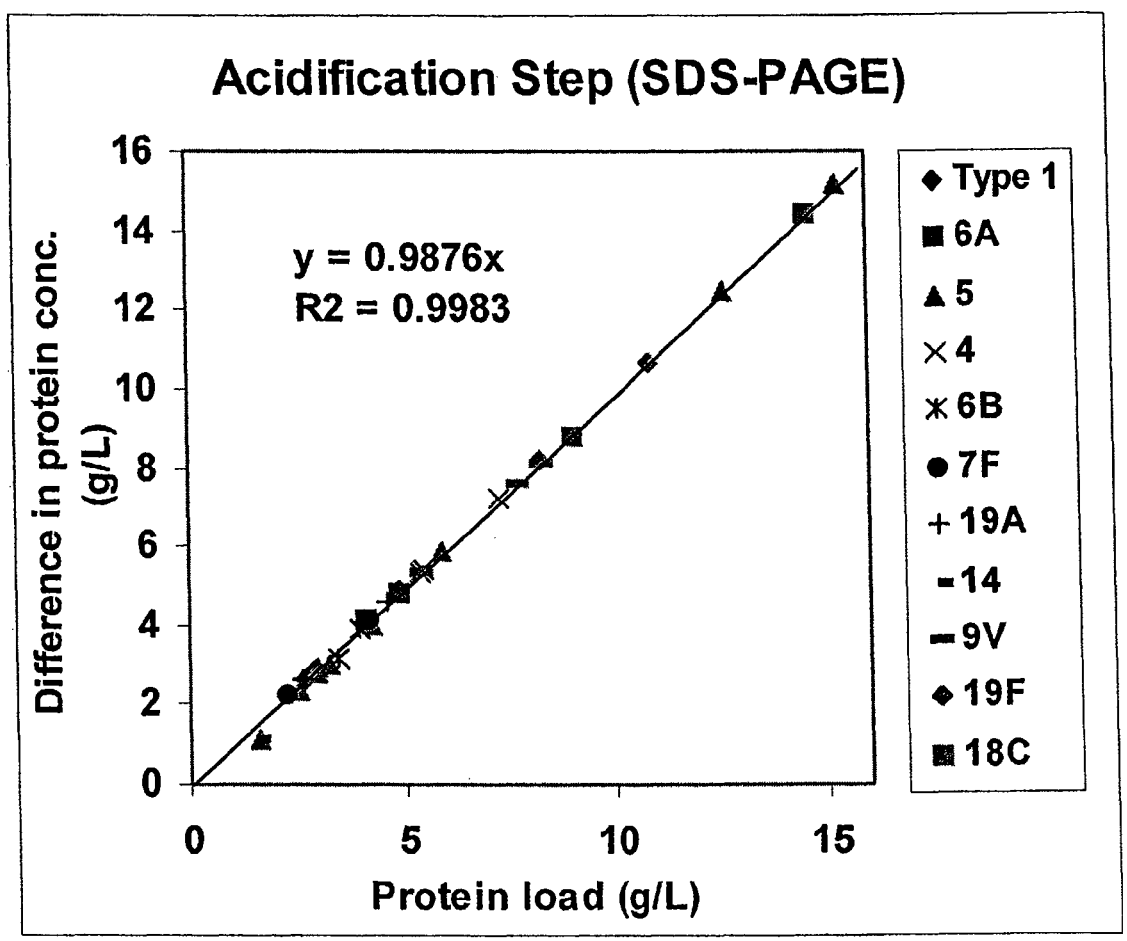
FIG. 13 shows protein removal efficiency attributable to the acidification step of the shortened purification process of the invention. The difference in protein concentration (SDS-PAGE) before and after acidification is plotted against initial protein concentration before acidification for batches of serotypes 1, 4, 5, 6A, 6B, 7F, 9V, 14, 18C, 19A, and 19F. The protein concentration difference divided by the initial protein concentration reflected the protein removal rate by the acidification step.

For purification of PnC polysaccharides, the most significant and difficult impurity to remove is proteins. To better understand the impurity removal efficiency of the shortened process, two of the major purification steps, acidification and activated carbon adsorption, were analyzed for protein removal. For the acidification step, the difference in protein concentration (SDS-PAGE) before and after acidification was plotted against the initial protein concentration before acidification for serotypes 1, 4, 5, 6A, 6B, 7F, 9V, 14, 18C, 19A, and 19F using the shortened purification process of the invention (FIG. 13).

Due to relatively small changes in solution volume before and after the acidification step, the protein concentration difference divided by the initial protein concentration reflected the protein removal rate by the acidification step. FIG. 13 shows the slope of the linear fit of protein concentration difference with respect to initial protein concentration (by SDS-PAGE assay). A very good linear relationship was observed between the protein concentration change and the initial concentration, with the $R^2$ close to 1. The slope was 0.9876, which corresponds to a 98.76% protein removal (assuming negligible solution volume change). Therefore, for all serotypes studied, the acidification step was very efficient and on average it removed more than 98% protein.

Figure 14:
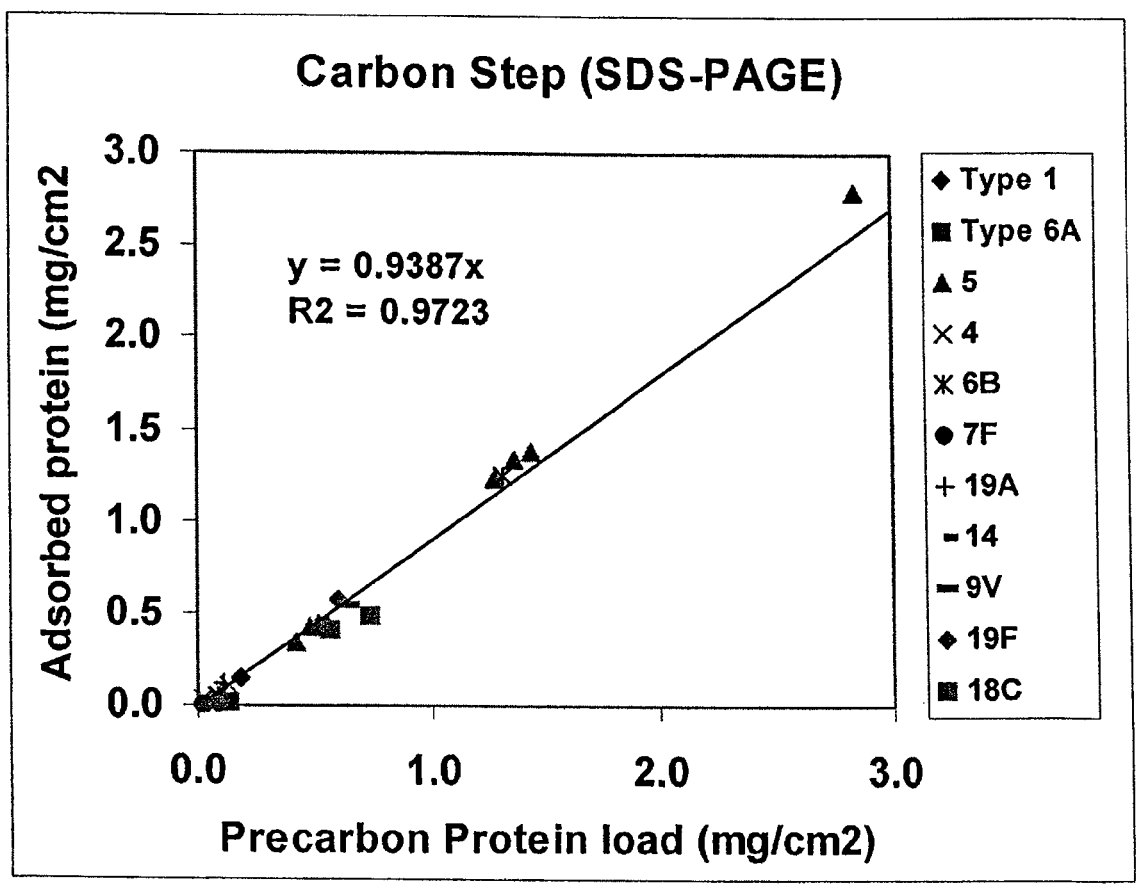
FIG. 14 shows protein removal efficiency attributable to the carbon adsorption step of the shortened purification process of the invention. The amount of protein removed (adsorbed on carbon) was plotted against initial protein loading amounts for batches of serotypes 1, 4, 5, 6A, 6B, 7F, 9V, 14, 18C, 19A, and 19F. The amount of protein removed divided by the initial protein loading amounts reflected the protein removal rate by the carbon adsorption step.

Similar to the acidification step, the efficiency of the activated carbon adsorption step was also evaluated by plotting the amount of protein removed (adsorbed on carbon) with respect to initial protein loading (FIG. 14). A good linear relationship between the removed protein and the initial protein loading was observed, although the $R^2$ (0.9723) was not as high as for the acidification step. Because the slope of this linear fit corresponds to the protein removal rate, the activated carbon adsorption step produced 93.87% protein removal.

Based on an analysis of the acidification and activated carbon adsorption steps, after the two steps only about 0.1% protein was left in the solution.

Conclusions for Examples 1-3

A shortened purification process was developed to replace the current purification process for capsular polysaccharides of *S. pneumoniae*. The shortened purification process was directly applied to serotypes 1, 4, 5, 6A, 6B, 7F, 9V, 14, 18C, and 19F, and to 19A with slight deviation. The process was conducted at 10 L scale using DOC-lysed fermentation broths. The impurity levels, including protein/PS, NA/PS and C-PS/PS ratios, all met their respective specifications. The PS yields were over 50% and comparable to that of the current purification process. In-process PS yield, protein/PS and NA/PS ratios were plotted to compare the behavior of different serotypes. Serotypes 1, 5, 9V, 19F, and 18C were found to be the most difficult to purify based on protein/PS ratios before and after the 100K UF/DF step.

Step analysis showed that the acidification and activated carbon adsorption steps removed more than 98% and 90% protein, respectively (as measured by SDS-PAGE).

Example 4

Substitution of Non-Animal Derived Lytic Agents for Deoxycholate Sodium in the Production of Polysaccharides The present example investigated whether non-animal derived lytic agents could be used as a substitute for deoxycholate sodium (DOC) within the process described above for the production of substantially purified capsular *Streptococcus pneumoniae* polysaccharides. As described above, DOC activates the LytA protein, which is an autolysin that is involved in cell wall growth and division in *Streptococcus* pneumoniae. The LytA protein has choline binding domains in its C-terminal portion, and mutations of the lytA gene are known to produce LytA mutants that are resistant to lysis with DOC.

A rapid microtiter plate assay was developed to identify compounds that cause cell lysis by a mechanism similar to that of DOC. Several non-animal derived alternatives to DOC were identified which were equally effective as DOC at killing *Streptococcus pneumoniae* cells and releasing polysaccharide. Following processing using standard conditions, the size and purity of the polysaccharides produced with the non-animal derived compounds were identical to those produced with DOC.

Methods

Cell Lysis: Compounds to be tested were added to fermentation broth at a final concentration of 0.1 to 0.01% (v/v) and the solution was allowed to incubate at 37° C. for one hour. The solution was then stored at 2-8° C. overnight. The following morning the solution was centrifuged to remove all cell debris. The cell-free broth was analyzed by SEC-HPLC to determine the concentration of released polysaccharide. The lysis could be performed at any temperature between 2-37° C., preferably at a pH range of 6.0-7.5. The concentration of the detergent was typically between 0.05-0.2% depending on the particular detergent.

Microtiter Assay: A rapid microtiter plate assay was devised for examining lytA-dependent lysis of pneumococci by different detergents or surfactants. Two pairs of isogenic strains of *S. pneumonoiae* were used in the assay; one member of each pair was wild type for the lytA gene while the other strain carried a deletion in the lytA gene Thus, if lysis were dependent on an active lytA function, that detergent would not lyse the mutant strains. The four strains, R6X, R6X, ΔlytA, D39 and D39 ΔlytA, were cultivated in HY-SOY®medium to approximately mid-log phase ($0D_{600}$ ~0.2-0.8; $OD_{600}$= Optical Density at 600 nm). Cells were then centrifuged and cell pellets were resuspended in HY-SOY® medium. To each well of the microtiter plate, 100 µL of cell suspension was added, along with 10 µL of detergent stocks or water as a control. After about 15 minutes at 36° C., the $OD_{600}$ of the samples was measured with a SPECTRA-MAX® spectrophotometer (Molecular Devices, Sunnyvale, Calif.). The following results were observed for freshly prepared cells or frozen and thawed cells: Wild-type cells exposed to DOC, sodium dodecyl sulfate, TRITON® X-100 and N-laurylsarcosine all had OD values comparable to the medium blank, which indicated that lysis had occurred. On the other hand, the ΔlytA cells did not lyse in the presence of these detergents, which indicates that LytA function is required for these detergents to lyse the cells.

Isolation of PS Used For Comparative Analytical Studies: Cultures were grown in HY-SOY® medium in 10 L bioreactors. The pH was controlled at around 7.0 using either NaOH or $Na_2CO_3$. At the end of growth (as indicated by no further increase in optical density), the cultures were treated with either 0.12% DOC or 0.1% NLS. The cultures were incubated for 12-16 hours. The effectiveness of cell killing was confirmed by plating a sample of treated broth on TSA-Blood Agar plates. Polysaccharide was purified from the clarified lysate using standard procedures (as described above). Purified polysaccharide was examined using a variety of standard analytical techniques appropriate to determine the purity and identity of the material.

The PS content of the lysate was determined using SEC-HPLC coupled to a refractive index (RI) detector.

Screening for Non-Animal Derived Lytic Agents Using Serotypes 1 and 6

*S. pneumoniae* serotypes 1 and 6B were separately grown in HY-SOY® based media, The cultures were separately harvested and separately dispensed into tubes. The non-animal derived compounds to be screened for lytic activity comparable to DOC were prepared as stock solutions (in suitable solvents) and added to the cultures. After overnight incubation, the tubes were centrifuged and the PS content of the lysates for each serotype were determined by SEC-H PLC and compared to DOC.

Screening for Non-Animal Derived Lytic Agents Using lytA Mutants

Isogenic pairs of strains containing the lytA mutation were grown in a HY-SOY® based medium. The cells were harvested and dispensed into wells in a microtiter plate. The test compound was added and the culture was incubated. After 15 min at 36° C., the optical density ($OD_{600}$) of each well was determined using a SPECTRAMAX® plate reader (Molecular Devices, Sunnyvale, Calif.)(see Tables 17 and 18, which summarize results from two separate tests for exemplary compounds).

TABLE 17

Change in Optical Density for lytA Mutant Strains (Test 1)

| Compound | Change in $OD_{600}$ | | | |
|---|---|---|---|---|
| | R6X | R6X ΔlytA | D39 | D39 ΔlytA |
| Blank | | | | |
| No addn | | | | |
| Deoxycholic acid, 0.1% | 100% | 34% | 99% | 47% |
| Lithocholic acid, 0.1% | 20% | 16% | 8% | -2% |
| Tauroglycocholic acid, 0.1% | 51% | -16% | 47% | -20% |
| Heptanoic acid, 0.1% | 25% | -57% | 7% | -30% |
| SDS, 0.1% | 99% | 28% | 95% | 36% |
| Octanesulfonic acid, 0.1% | 43% | 6% | 34% | 16% |
| TRITON ® X-100, 0.1% | 91% | 22% | 97% | 30% |
| TWEEN ® 80, 0.1% | 36% | 14% | 20% | 19% |
| TWEEN ® 20, 0.1% | 44% | 22% | 28% | 19% |
| N-lauryl sarcosine, 0.1% | 100% | -34% | 89% | -44% |
| PLURONIC ® L31, 0.1% | 39% | 0% | 17% | -38% |
| PLURONIC ® L-61, 0.1% | 23% | -3% | -19% | 14% |
| PLURONIC ® L81, 0.1% | 21% | -3% | -14% | 10% |
| ANTAROX ® 17-R-2, 0.1% | 37% | 24% | 7% | 16% |

TABLE 18

Change in Optical Density for lytA Mutant Strains (Test 2)

| Compound | Change in $OD_{600}$ | | | |
|---|---|---|---|---|
| | R6X | R6X ΔlytA | D39 | D39 ΔlytA |
| Blank | | | | |
| No addn | | | | |
| Water | -8% | -8% | 3% | -8% |
| Deoxycholic acid, 0.1% | 103% | 20% | 101% | 41% |
| SDS, 0.1% | 102% | -13% | 100% | 16% |
| N-lauryl sarcosine, 0.1% | 102% | -40% | 101% | 14% |
| TRITON ® X-100, 0.1% | 101% | -19% | 100% | 4% |
| TWEEN ® 20, 0.1% | 6% | -17% | -5% | -3% |
| Octanesulfonic acid, 0.1% | 13% | 3% | 18% | -3% |

Based on the screening studies described above, the following non-animal derived lytic agent alternatives to DOC were identified: decanesulfonic acid, IGEPAL® CA-630 (tert-Octylphenoxy poly(oxyethylene)ethanol; CAS #: 9002-93-1; available from Sigma Aldrich., St. Louis, Mo.), N-lauryl sarcosine sodium (NLS), lauryl iminodipropionate, sodium dodecyl sulfate, TRITON® X-100, chenodeoxycholate, hyodeoxycholate, glycodeoxycholate, taurodeoxcholate, taurochenodeoxycholate, and cholate.

Comparison of DOC-Lysed PS to NLS-Lysed PS

*S. pneumoniae* polysaccharide serotypes 1, 4, 5, 6A, 6B, and 7F were purified at the 10 L scale as described above in Examples 1 and 2 using the improved process of the present invention. However, in one group NLS (0.1%) was used as the lytic agent while in another group DOC (0.12%) was used as the lytic agent.

PS yield, protein/PS ratios, NA/PS ratios, and PS molecular weight were measured as described above, and results are summarized in Table 19. These results showed that the use of NLS as a lytic agent within the purification methods of the invention produced relatively high PS yields with relatively low protein and nucleic acid levels. In fact, for the majority of serotypes tested, use of NLS as a lytic agent produced higher PS yields compared to the use of DOC.

TABLE 19

PS Characterization For Different Serotypes Using DOC vs. NLS

| Serotype | Lytic Agent | PS Yield (%) | Protein/PS (%) | Nucleic Acid/PS (%) | SEC MALLS MW (g/mol, $10^6$) |
|---|---|---|---|---|---|
| 1 | 0.12% DOC | 20% | 4.2% | 0.04% | 0.615 |
| 1 | 0.1% NLS | 41% | 2% | 0.04% | 0.65 |
| 4 | 0.12% DOC | 72% | 0.05% | 0.02% | 0.38 |
| 4 | 0.1% NLS | 57% | 0.67% | 0.25% | 0.34 |
| 5 | 0.12% DOC | 57% | 3.6% | 0.18% | 0.32 |
| 5 | 0.1% NLS | 63% | 1.8% | 0.01% | 0.35 |
| 6A | 0.12% DOC | 56% | 0.7% | 0.00% | 0.55 |
| 6A | 0.1% NLS | 66% | 1.1% | 0.05% | 0.43 |
| 6B | 0.12% DOC | 38% | 0.6% | 0.05% | 0.969 |
| 6B | 0.1% NLS | 55% | 0.1% | 0.01% | 1.0 |
| 7F | 0.12% DOC | 73% | 0.7% | 0.06% | 0.814 |
| 7F | 0.1% NLS | 76% | 0.5% | 0.02% | 0.912 |

TABLE 19-continued

PS Characterization For Different Serotypes Using DOC vs. NLS

| Serotype | Lytic Agent | PS Yield (%) | Protein/PS (%) | Nucleic Acid/PS (%) | SEC MALLS MW (g/mol, $10^6$) |
|---|---|---|---|---|---|

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A clarified and acidified retentate solution of pH less than 4.5 comprising capsular polysaccharides from a cell lysate of a *Streptococcus pneumoniae* serotype selected from the group consisting of 1, 4, 5, 6A, 6B, 7F, 9V, 14, 18C, 19A, 19F, and 23F, wherein more than 98% of protein has been removed from the solution compared to the cell lysate.

2. A clarified and acidified retentate solution of pH less than 4.5 comprising capsular polysaccharides from a *Streptococcus pneumoniae* serotype 19A cell lysate, wherein more than 98% of protein has been removed from the solution compared to the cell lysate.

3. The solution according to claim 2, wherein said capsular polysaccharides have a molecular weight of 488,000 daltons to 525,000 daltons.

* * * * *